US012409183B2

(12) United States Patent
Christal et al.

(10) Patent No.: US 12,409,183 B2
(45) Date of Patent: Sep. 9, 2025

(54) METHOD OF USING ILOPROST FOR TREATING FROSTBITE

(71) Applicant: BTG INTERNATIONAL INC., West Conshohocken, PA (US)

(72) Inventors: Kevin A. Christal, Burlingame, CA (US); Christa-Lynn J. Vampola, Los Altos, CA (US); Wade W. Benton, Emerald Hills, CA (US)

(73) Assignee: BTG INTERNATIONAL INC., West Conshohocken, PA (US)

( * ) Notice: Subject to any disclaimer, the term of this patent is extended or adjusted under 35 U.S.C. 154(b) by 0 days.

(21) Appl. No.: 18/776,438

(22) Filed: Jul. 18, 2024

(65) Prior Publication Data

US 2025/0099484 A1    Mar. 27, 2025

Related U.S. Application Data

(60) Provisional application No. 63/514,244, filed on Jul. 18, 2023.

(51) Int. Cl.
*A61K 31/5578* (2006.01)
*A61P 17/02* (2006.01)

(52) U.S. Cl.
CPC .......... *A61K 31/5578* (2013.01); *A61P 17/02* (2018.01)

(58) Field of Classification Search
CPC ............................ A61K 31/5578; A61P 17/02
See application file for complete search history.

(56) References Cited

U.S. PATENT DOCUMENTS

| | | | |
|---|---|---|---|
| 5,523,321 | A | 6/1996 | Stuerzebecher et al. |
| 9,517,202 | B2 | 12/2016 | Chen et al. |
| 2006/0147520 | A1 | 7/2006 | Ruegg |
| 2006/0276546 | A1 | 12/2006 | Keith et al. |
| 2009/0215769 | A1 | 8/2009 | Krahn et al. |
| 2012/0321579 | A1 | 12/2012 | Edelson et al. |
| 2013/0040898 | A1 | 2/2013 | Johansson |
| 2014/0200274 | A1 | 7/2014 | Frank et al. |
| 2016/0206661 | A1 | 7/2016 | Fraser et al. |
| 2019/0015397 | A1 | 1/2019 | Truchetet et al. |
| 2019/0307834 | A1 | 10/2019 | Sekar et al. |

FOREIGN PATENT DOCUMENTS

| | | |
|---|---|---|
| WO | WO-2022032141 A1 | 2/2022 |
| WO | WO-2022036234 A1 | 2/2022 |

OTHER PUBLICATIONS

Abraham et al., "Optimal management of digital ulcers in systemic sclerosis," Ther Clin Risk Manag. Jun. 15, 2015;11:939-47. eCollection 2015.

Actelion Pharmaceuticals US, I. (2013). Ventavis (iloprost) Inhalation Solution Prescribing Information (San Francisco, CA), issued Nov. 2013, 24 pages.
Actelion Pharmaceuticals US, I. (2019). Ventavis (iloprost) Inhalation Solution Prescribing Information (San Francisco, CA), Dec. 2019, 22 pages.
Actelion Pharmaceuticals US, Inc. 2017, VENTAVIS (iloprost). [inhalation solution prescribing information]. San Francisco, CA. 23 pages, Oct. 2017.
Actelion Pharmaceuticals US, Inc. (2022). Ventavis (iloprost) inhalation solution, for oral inhalation use Prescribing Information (NDA 021779) (San Francisco, CA), 22 pages. https://www.accessdata.fda.gov/drugsatfda_docs/label/2022/021779s021lbl.pdf. Mar. 25, 2022.
Afssaps, Medicines containing buflomedil: Suspension of marketing authorisation—Press release, Médicaments contenant du buflomedil: Suspension de l'autorisation de mise sur le marché—Communiqué [en ligne]. Disponible sur: http://www.afssaps.fr/Infos-de-securite/ Communiques-Points-presse/Medicaments-contenant-du-buflomedil-Suspension-de- l-autorisation-de-mise-sur-le-marche-Communique. Feb. 2, 2011, 4 pages including English translation.
Al Yafi, "Using Intra-arterial tPA for Severe Frostbite Cases. An Observational Comparative Retrospective Study," J Burn Care Res. 2019;40(6):907-912.
Archer et al., ZK 36-374, a stable analog of prostacyclin, prevents acute hypoxic pulmonary hypertension in the dog. J Am Coll. Cardiol. 8:1189-1194 (1986).
Armstrong et al., Functional and ligand binding studies suggest heterogeneity of platelet prostacyclin receptors. Br J Pharmacol 97, 657-668 (1989).
Bagis et al., Effect of iloprost on contractile impairment and mitochondrial degeneration in ischemia-reperfusion of skeletal muscle. Physiology international 105:61-75 (2018).
Bali et al., "Discontinuing long-term Iloprost treatment for Raynaud's Phenomenon and systemic sclerosis. A single-center, randomized, placebo-controlled, double-blind study. Acta dermatovenerologica Alpina," Acta Dermatovenerol Alp Pannonica Adriat. 2011;20(1):13-21.
Barnes et al., "Epidemiology of systemic sclerosis: incidence, prevalence, survival, risk factors, malignancy, and environmental triggers," Curr Opin Rheumatol. Mar. 2012;24(2):165-70.
Baron et al., "Consensus opinion of a North American Working Group regarding the classification of digital ulcers in systemic sclerosis," Clin Rheumatol. 2014;33(2):207-214. Epub Dec. 20, 2013.
Battenfeld, "Studies on reproductive toxicity of iloprost in rats, rabbits and monkeys," Toxicol Lett 78, 223-234 (1995).
Bayer New Zealand Limited (2019). Ilomedin (iloprost) solution for infusion New Zealand Data Sheet (North Shore, Auckland, New Zealand). http://www.medsafe.govt.nz/profs/datasheet/i/Ilomedininf.pdf, dated Dec. 5, 2019, 13 pages.
Bellando-Randone et al., The safety of iloprost in systemic sclerosis in a real-life experience. Clin Rheumatol 37:1249-1255 (2018).
Bertele et al., "Defective fibrinolytic response in atherosclerotic patients—effect of iloprost and its possible mechanism of action," Thromb.Haemost. 60:141-144 (1988).

(Continued)

*Primary Examiner* — Sahar Javanmard
(74) *Attorney, Agent, or Firm* — Troutman Pepper Locke LLP

(57) ABSTRACT

The present disclosure generally relates to treatment of frostbite by intravenous injection or intravenous infusion of iloprost or a pharmaceutically acceptable salt thereof.

28 Claims, 4 Drawing Sheets

(56) References Cited

OTHER PUBLICATIONS

Bettoni et al, Systemic sclerosis therapy with iloprost. A prospective observational study of 30 patients treated for a median of 3 years, Clin Rheumatol 21:244-250 (2002).
Biasi et al., Iloprost as cyclic five-day infusions in the treatment of scleroderma. An open pilot study in 20 patients treated for one year. Rev. Rhum. Engl. Ed 65:745-750 (1998).
Blake et al., Quantitative studies of bone in postmenopausal women using (18)F-fluoride and (99m) Tc-methylene diphosphonate.J. Nucl. Med. 43:338-345 (2002).
Boulas, "Amputations of the fingers and hand. Indications for replantation," The Journal of the American Academy of Orthopaedic Surgeons 6, 100-105 (1998).
Bouskela et al., "Affects of buflomedil on spontaneous vasomotion and mean arteriolar internal diameter in the hamster cheek pouch," Journal of vascular research 31, 287-294 (1994).
Boxer et al., Inhibition of polymorphonuclear leukocyte adherence by prostacyclin. J Lab Clin. Med 95, 672-678 (1980).
Bruen, "Reduction of the incidence of amputation in frostbite injury with thrombolytic therapy," Arch. Surg 142, 546-51; discussion 551-3 (2007).
Campbell et al., "Pathogenesis of systemic sclerosis: a vascular hypothesis," Semin Arthritis Rheum. 1975;4(4):351-368.
Cappelli et al., "Management of Raynaud phenomenon and digital ulcers in scleroderma," Rheum Dis Clin North Am. 2015;41(3):419-438.
Caramaschi et al., "Evaluation of finger skin temperature in scleroderma patients cyclically treated with iloprost.," Joint Bone Spine. 2006;73(1):57-61. Epub Sep. 16, 2005.
Carceller et al., "Amputation Risk Factors in Severely Frostbitten Patients," International journal of environmental research and public health Apr. 15, 2019;16(8):1351, 8 pages.
Carmichael, "Remote Delivery of Thrombolytics Prior to Transfer to a Regional Burn Center for Tissue Salvage in Frostbite. A Single-center Experience of 199 Patients," Journal of burn care & research: official publication of the American Burn Association 43:54-60 (2022).
Carpentier, "Norepinephrine, phentolamine and buflomedil influence n arteriolar vasomotion in the hamster skinfold preparation," Blood vessels 28 Suppl 1, 33-37 (1991).
Cauchy et al., "A Controlled Trial of a Prostacyclin and rt-PA in the Treatment of Severe Frostbite," N Eengl J Med 364:189-190 (Jan. 13, 2011).
Cauchy et al., "A New Proposal for Management of Severe Frostbite in the Austere Environment," Wilderness & environmental medicine 27:92-99 (2016).
Cauchy et al., "Retrospective study of 70 cases of severe frostbite lesions," A proposed new classification scheme. Wilderness & environmental medicine 1:248-255 (2001).
Cauchy et al., Supplement; A controlled trial of a prostacyclin and rt-PA in the treatment of severe frostbite. N Engl J Med 2011;364:189-90, 2 pages.
Cauchy et al., "The role of bone scanning in severe frostbite of the extremities. A retrospective study of 88 cases," European journal of nuclear medicine 27:497-502 (2000a).
Cauchy, "The value of technetium 99 scintigraphy in the prognosis of amputation in severe frostbite injuries of the extremities. A retrospective study of 92 severe frostbite injuries," The Journal of hand surgery 25:969-978 (2000).
CDER (2004). Clinical Pharmacology and Biopharmaceutics Review(s), Part 2: In Drug Approval Package for Ventavis (iloprost) inhalation solution, for oral inhalation use (NDA 021779), 108 pages. https://www.accessdata.fda.gov/drugsatfda_docs/nda/2004/21-779_Ventavis_biopharmr_P2.pdf. Nov. 8, 2021.
CDER (2004b). Pharmacology Review(s): In Drug Approval Package for Ventavis (iloprost), 202 pages. https://www.accessdata.fda.gov/drugsatfda_docs/nda/2004/21-779_Ventavis_pharmr.pdf. Nov. 8, 2021.

Ceru et al., "Effects of five-day versus one-day infusion of iloprost on the peripheral microcirculation in patients with systemic sclerosis," Clinical and Experimental Rheumatology 15:381-385 (1997).
Cestelli et al., "Effect of treatment with iloprost with or without bosentan on nailfold video capillaroscopic alterations in patients with systemic sclerosis," Modern rheumatology 27, 110-114 (2017).
Cheguillaume, Benoit, "Controlled trial of iloprost and rt-PA in the treatment of severe frostbite," Human Medicine and Pathology, 71 pages (Jun. 21, 2011).
Chung and Fiorentino, "Digital ulcers in patients with systemic sclerosis," Autoimmun Rev. Feb. 2006;5(2):125-128. Epub Sep. 13, 2005.
Chung et al., "Combined administration of nitric oxide gas and iloprost during cardiopulmonary bypass reduces platelet dysfunction," A pilot clinical study. J Thorac. Cardiovasc. Surg. 129:782-790 (2005).
Colaci et al., "Long-term treatment of scleroderma-related digital ulcers with iloprost. A cohort study," Clinical and experimental rheumatology 35 Suppl 106:179-183 (2017).
Co-pending U.S. Appl. No. 18/260,778, inventors Benton; Wade W. et al., filed on Jul. 7, 2023.
Co-pending U.S. Appl. No. 18/260,779, inventors Benton; Wade W. et al., filed on Jul. 7, 2023.
CoTherix, Inc. (2004) Drug Approval Package for Ventavis (iloprost) inhalation solution, for oral inhalation use (NDA 021779). Clinical Pharmacology and Biopharmaceutics Review(s), Part 2. https://www.accessdata.fda.gov/drugsatfda_docs/nda/2004/21-779_Ventavis_biopharmr_P2.pdf. Nov. 8, 2021, 108 pages.
CoTherix, Inc. (2004). Drug Approval Package for Ventavis (iloprost) inhalation solution, for oral inhalation use (NDA 021779). Pharmacology Review(s). In https://www.accessdata.fda.gov/drugsatfda_docs/nda/2004/21-779_Ventavis_pharmr.pdf. Nov. 8, 2021, 202 pages.
Cowley et al., "Effects of Prostacyclin and of the Stable Prostacyclin Analogue ZK 36374 on Forearm Blood Flow and Blood Platelet Behaviour in Man," Thrombosis and Haemostasis 1985, pp. 90-94.
Crooks et al., "Effectiveness of intravenous prostaglandin to reduce digital amputations from frostbite: an observational study," Canadian Journal of Emergency Med. Epub Jul. 23, 2022, 8 pages.
Crooks et al., Supplement 1 to "Effectiveness of intravenous prostaglandin to reduce digital amputations from frostbite: an observational study," Canadian Journal of Emergency Med. Epub Jul. 23, 2022,1 page (2022).
Crooks et al., Supplement 2 to "Effectiveness of intravenous prostaglandin to reduce digital amputations from frostbite: an observational study," Canadian Journal of Emergency Med. 24:622-629) Epub Jul. 23, 2022, 8 pages (2022).
Cutolo et al., "Longterm treatment with endothelin receptor antagonist bosentan and iloprost improves fingertip blood perfusion in systemic sclerosis," The Journal of rheumatology 41:881-886 (2014).
Czeslick et al., "Inhibition of intracellular tumour necrosis factor (TNF)-alpha and interleukin (IL)-6 production in human monocytes by iloprost," Eur J Clin Inves. 2003;33(11):1013-1017.
D'Amelio et al., "Iloprost modulates the immune response in systemic sclerosis," BMC Immunol. 2010;11:62, 8 pages.
De Putter et al., "Economic impact of hand and wrist injuries. Health-care costs and productivity costs in a population-based study," The Journal of bone and joint surgery. American vol. 94, e56 (2012).
Della Bella et al., "Cytokine production in scleroderma patients. Effects of therapy with either iloprost or nifedipine," Clinical and experimental rheumatology 15, 135-141 (1997).
Denton et al., "Systemic sclerosis," Lancet. 2017;390(10103):1685-1699.
Dowd et al., "Effect of prostaglandins 12 and E1 on red cell deformability in patients with Raynaud's phenomenon and systemic sclerosis," Br Med J (Clin Res. Ed) 283, 350 (1981).
Downs, "The feasibility of creating a checklist for the assessment of the methodological quality both of randomised and non-randomised studies of health care interventions," J Epidemiol Community Health. 1998;52(6):377-384.
Edlich et al., "Cold injuries," Compr Ther 15, 13-21 (1989).

(56) References Cited

OTHER PUBLICATIONS

Edmonson et al., "Abstract No. 52: Intra-Arterial Thrombolytic Therapy for Limb Salvage in Severe Frostbite," Scientific Session 6 | Arterial Lysis, Arterial Imaging| vol. 19, Issue 2, Supplement , S21-S22, Feb. 2008.
Endorf et al., "Biopsychosocial factors associated with complications in patients with frostbite," Medicine 2022;101:34(e30211), pp. 1-5.
Endorf et al., "Socioeconomic and comorbid factors associated with frostbite injury in the United States," J Burn Care Res. May 17, 2022;43(3):646-651.
Ercan et al., The relaxing activity of iloprost and prostaglandin E2 in the isolated various smooth muscle strips of the rabbit. Pharmacology. 1985;31(2):61-66.
Ervasti et al., "Sequelae of moderate finger frostbite as assessed by subjective sensations, clinical signs, and thermophysiological responses," Int. J Circumpolar. Health 59, 137-145 (2000).
Fabian et al., " A retrospective cohort study examining treatments and operative interventions for frostbite in a tertiary care hospital," CJEM 19, 88-95 (2017).
Ferri et al., "Systemic sclerosis: demographic, clinical, and serologic features and survival in 1,012 Italian patients," Medicine (Baltimore). Mar. 2002;81(2):139-53.
Ffoti et al., "Long-term clinical stabilization of scleroderma patients treated with a chronic and intensive IV iloprost regimen," Rhematol Int 2017;37(2):245-249.
Fisher et al., "Comparison of equimolar concentrations of iloprost, prostacyclin, and prostaglandin E1 on human platelet function," J Lab Clin Med 109, 184-190 (1987).
Freedman et al., "Nitric Oxide and Superoxide Detection in Human Platelets," Methods in Enzymology, vol. 301, 10 pages (1999).
Fudge, "Preventing and Managing Hypothermia and Frostbite Injury," Sports health 8:133-139 (2016).
Galanakos et al., "Psychological and social consequences after reconstruction of upper extremity trauma," Methods of detection and management. Journal of reconstructive microsurgery 30, 193-206 (2014).
Garcia de la Peña Lefebvre et al, "Efficacy of Raynaud's Phenomenon and digital ulcer pharmacological treatment in systemic sclerosis patients: a systematic literature review," Rheumatol Int 2015;35(9):1447-1459.
Garner et al., "Prevalence, risk factors and associations of primary Raynaud's phenomenon: systematic review and meta-analysis of observational studies," BMJ Open. 2015;5(3):e006389, pp. 1-9.
Gomez-Arronyo et al., "Iloprost reverses established fibrosis in experimental right ventricular failure," Eur Respir J 2015;45(2):449-462.
Grant et al., "Iloprost. A review of its pharmacodynamic and pharmacokinetic properties, and therapeutic potential in peripheral vascular disease, myocardial ischaemia and extracorporeal circulation procedures," Drugs. 1992;43(6):889-924.
Greenwald et al., "An algorithm for early aggressive treatment of frostbite with limb salvage directed by triple-phase scanning," Plast. Reconstr. Surg. 102, 1069-1074 (1998).
Groechenig, Treatment of frostbite with iloprost. Lancet 344, 1152-1153 (1994).
Haberey et al., "Hemodynamic profile of iloprost in rats, rabbits, and cats. In Prostacyclin and its stable analogue iloprost," R.J. Gryglewski and G. Stock, eds. (Berlin (Germany): Springer-Verlag), pp. 151-158 (1987).
Hachulla et al., "Natural history of ischemic digital ulcers in systemic sclerosis: single-center retrospective longitudinal study," J Rheumatol Dec. 2007;34(12):2423-30. Epub Nov. 1, 2007.
Handford et al., "Frostbite. A practical approach to hospital management," Extreme physiology & medicine 3:7,10 pages (2014).
Hannah, "Psychosocial issues after a traumatic hand injury. Facilitating adjustment. Journal of hand therapy," Official journal of the American Society of Hand Therapists 24, 95-102; quiz 103 (2011).
Haye-Legrand et al., "Relaxation of isolated human pulmonary muscle preparations with prostacyclin (PGI2) and its analogs," Prostaglandins 33, 845-854 (1987).
Herman et al., "Critical evaluation of the in vivo selectivity between hypotensive and platelet antiaggregating actions of iloprost and prostacyclin in beagle dogs," Arch. Int. Pharmacodyn. Ther. 300, 281-291 (1989).
Herrick, Raynaud's phenomenon (secondary), BMJ Clin Evid. 2008; 09:1125, 34 pages. Published online Sep. 26, 2008.
Hickey et al., Guidelines for Thrombolytic Therapy for Frostbite. Journal of burn care & research, Official publication of the American Burn Association 41, 176-183 (2020).
Hildebrand et al., "Pharmacokinetics of iloprost in patients with chronic renal failure and on maintenance haemodialysis," Int J Clin Pharmacol Res. 1990;10(5):285-292.
Hildebrand et al., "Pharmacokinetics of iloprost in patients with hepatic dysfunction," Int J Clin Pharmacol Ther Toxicol. 1990;28(10):430-434.
Hildebrand et al., "Pharmacokinetics of iloprost in patients with severe peripheral arterial occlusive disease," Eicosanoids. 1990;3(3):145-148.
Hildebrand, "Pharmacokinetics of iloprost and cicaprost in mice," Prostaglandins 44:431-442 (1992).
Hinchcliff et al., "Systemic sclerosis/scleroderma: a treatable multisystem disease," Am Fam Physician. 2008;78(8):961-968.
Hughes et al., "Digital ulcers in systemic sclerosis," Rheumatology (Oxford). 2017;56(1):14-25.
Hummers et al., "Management of Raynaud's phenomenon and digital ischemic lesions in scleroderma," Rheum Dis Clin North Am. May 2003;29(2):293-313.
Hutchinson, "Frostbite of the hand," The Journal of hand surgery 39:1863-1868 (2014).
Ilomedin Data Sheet by Bayer, dated Mar. 19, 2012, 13 pages.
Imray et al., "Cold damage to the extremities. Frostbite and non-freezing cold injuries," Postgraduate medical journal 85:481-488 (2009).
International Preliminary Report on Patentability for International Application No. PCT/US2021/045013 dated Feb. 16, 2023, 13 pages.
International Preliminary Report on Patentability for International Application No. PCT/US2021/045963 dated Feb. 23, 2023, 8 pages.
International Search Report and Written Opinion for International Application No. PCT/US2021/045013 dated Dec. 21, 2021, 18 pages.
International Search Report for International Patent Application PCT/US2021/045963, mailed on Nov. 22, 2021, 14 pages.
Ioannou et al., "Platelet antiaggregatory substances inhibit arachidonic acid induced coronary constriction," Can J Physiol Pharmacol 64(4):398-405 (1986).
Kahaleh, "Endothelin, an endothelial-dependent vasoconstrictor in scleroderma. Enhanced production and profibrotic action," Arthritis Rheum. Aug. 1991;34(8):978-83. doi: 10.1002/art.1780340807.
Kawald et al., "Low versus high-dose iloprost therapy over 21 days in patients with secondary Raynaud's phenomenon and systemic sclerosis: a randomized, open, single-center study," J Rheumatol. 2008;35(9):1830-1837.
Keller et al., "Behandlung des Raynaud-Phänomens bei Sklerodermie-Patienten mit einem neuen stabilen Prostacyclin-Derivat," [Treatment of Raynaud's phenomenon in scleroderma with a new stable prostacyclin derivative] Dtsch Med Wochenschr 1984; 109(38): 1433-1438, 1 page English Abstract only.
Khanna et al., Effect of Macitentan on the Development of New Ischemic Digital Ulcers in Patients With Systemic Sclerosis DUAL-1 and DUAL-2 Randomized Clinical Trials. JAMA. 2016;315(18):1975-1988.
Koljonen et al., "Frostbite injuries treated in the Helsinki area from 1995 to 2002," The Journal of trauma 57:1315-1320 (2004).
Kowal-Bielecka et al., "Update of EULAR recommendations for the treatment of systemic sclerosis," Ann Rheum Dis. 2017;76(8):1327-1339.

(56) References Cited

OTHER PUBLICATIONS

Krause et al., "Pharmacokinetics and biotransformation of the prostacyclin analogue, ZK 36 374, in the monkey (*Macaca fascicularis*)," Prostaglandins, leukotrienes, and medicine 11, 325-338 (1983).
Krause et al., "Pharmacokinetics and Pharmacodynamics of Radio-Labeled Iloprost in Elderly Volunteers", European Journal of Clinical Pharmacology, 1987, vol. 32, pp. 597-605.
Krause, "Pharmacokinetics and Pharmacodynamics of the Prostacyclin Analogue Iloprost in Man," Eur. J. Clin. Pharmacol 30:61-68 (1986).
Krause, W., "Pharmacokinetics and biotransformation of the prostacyclin analogue, ZK 36 374, in the beagle dog," Prostaglandins, leukotrienes, and medicine 13, 143-151 (1984).
Kyle et al., "Placebo controlled study showing therapeutic benefit of iloprost in the treatment of Raynaud's Phenomenon," J Rheumatol. 19:1403-1406 (1992).
Lacey et al., "An Institutional Protocol for the Treatment of Severe Frostbite Injury-A 6-Year Retrospective Analysis. Journal of burn care & research," Official publication of the American Burn Association 42:817-820 (2021).
Leroy et al., "Scleroderma (systemic sclerosis): classification, subsets and pathogenesis," J Rheumatol. Feb. 15(2):202-205 (1988).
Leroy, "Systemic sclerosis. A vascular perspective," Rheum Dis Clin North Am. 1996;22(4):675-694.
Levien et al., "Advances in the treatment of Raynaud's phenomenon," Vasc Health Risk Manag. 2010;6:167-177.
Limjeerajarus et al., "Characterization of a Thermo-Sensitive Injectable Hydrogel as an Iloprost Delivery System for Dental Use", Key Engineering Materials, Aug. 3, 2020, vol. 856, pp. 391-398.
Lindemann et al., "Prostacyclin inhibits adhesion of polymorphonuclear leukocytes to human vascular endothelial cells due to adhesion molecule independent regulatory mechanisms," Basic Res.Cardiol. 98: 8-15 (2003).
Linford et al., "The evolution of the Helsinki frostbite management protocol," Burns: Journal of the International Society for Burn Injuries 43, 1455-1463 (2017).
Lorentzen et al., "Interventions for frostbite injuries," Cochrane Database Syst Rev. 12:CD012980, 44 pages (2020).
Lye et al., "Effect of iloprost (ZK36374) and prostacyclin on in vitro human cerebral arteries," Br J Pharmacol 1986;89:691, 1 page.
Magnum et al., Hyperbaric Oxygen Therapy with Iloprost Improves Di it Salvage in Severe Frostbite Compared to Iloprost Alone. Medicina (Kaunas, Lithuania) 57, 11 pages. (2021).
Majed et al., "Molecular mechanisms regulating the vascular prostacyclin pathways and their adaptation during pregnancy and in the newborn," Pharmacological reviews 64:540-582 (2012).
Marsigny, "Mountain frostbite," The Newsletter of the International Society for Mountain Medicine 1998;8(3):8-10.
Matucci-Cerinic, " Digital ulcers and outcomes assessment in scleroderma," Rheumatology (Oxford). 2008;47(Suppl5):v46-47.
Matucci-Cerinic et al., "Elucidating the burden of recurrent and chronic digital ulcers in systemic sclerosis: long-term results from the DUO Registry," Ann Rheum Dis. Oct. 2016;75(10):1770-1776. Epub Nov. 26, 2015.
Matucci-Cerinic et al., "Review: evidence that systemic sclerosis is a vascular disease," Arthritis Rheum. Aug. 2013;65(8):1953-1962.
Mayes et al., "Endothelin and endothelin receptor antagonists in systemic rheumatic disease," Arthritis and Rheum. 2003;48(5):1190-1199.
Mchugh et al., "Infusion of iloprost, a prostacyclin analogue, for treatment of Raynaud's phenomenon in systemic sclerosis," Ann Rheum Dis 47:43-47 (1988).
Mcintosh et al., "Wilderness Medical Society Clinical Practice Guidelines for the Prevention and Treatment of Frostbite," 2019 Update. Wilderness & environmental medicine 30, S19-S32 (2019).
Mcmahon et al., "Cold weather issues in sideline and event management," Current sports medicine reports 11:135-141 (2012).
Medsger, "Epidemiology of systemic sclerosis," Clin Dermatol. Apr.-Jun. 1994;12(2):207-16.
Mehta et al., "Frostbite injury. Prediction of tissue viability with triple-phase bone scanning," Radiology 170:511-514 (1989).
Merkel et al., "Measuring disease activity and functional status in patients with scleroderma and Raynaud's Phenomenon," Arthritis Rheum. 2002;46(9):2410-2420.
Milio et al., "Iloprost treatment in patients with Raynaud's phenomenon secondary to systemic sclerosis and the quality of life. A new therapeutic protocol," Rheumatology. (Oxford) 45, 999-1004 (2006).
Millett et al., "Frostbite. Spectrum of Imaging Findings and Guidelines for Management," Radiographics 36, 2154-2169 (2016).
Mills et al., Frostbite. Experience with rapid rewarming and ultrasonic therapy. Part III. 1961. Alaska med cine 35:19-27 (1993).
Modesti et al., "Acute reversible reduction of PGI platelet receptors after iloprost infusion in man," Thromb Res. 1987:48(6):663-669.
Mohr et al., "Cold injury," Hand clinics 25:481-496 (2009).
Morton et al., Quantitative Synthesis—An Update. Methods Guide for Comparative Effectiveness Reviews. 70 pages. (Prepared by the Scientific Resource Center under Contract No. 290-2012-0004-C). Rockville, MD: Agency for Healthcare Research and Quality; Feb. 2018.
Mouthon et al., "Impact of digital ulcers on disability and health-related quality of life in systemic sclerosis," Ann Rheum Dis. Jan. 2010;69(1):214-217.
Musial et al., "Fibrinolytic activity of prostacyclin and iloprost in patients with peripheral arterial disease," Prostaglandins 31:61-70 (1986).
Negrini et al., "Ioprost use and medical management of systemic sclerosis-related vasculopathy in Italian tertiary referral centers: results from the PROSIT study," Clinical and experimental medicine 19, 357-366 (2019).
Nicolini et al., "Inhibitory effect of unstimulated neutrophils on platelet aggregation by release of a factor similar to endothelium-derived relaxing factor (EDRF)," Biochem Pharmacol. 1990;40(10):2265-2269.
Nihtyanova et al., "Clinical burden of digital vasculopathy in limited and diffuse cutaneous systemic sclerosis," Ann Rheum Dis. Jan. 2008;67(1):120-3. Epub Jul. 27, 2007.
Nygaard et al., "Time Matters in Severe Frostbite. Assessment of Limb/Digit Salvage on the Individual Patient Level," Journal of burn care & research : official publication of the American Burn Association 38:53-59 (2017).
Olschewski et al., "Pharmacodynamics and pharmacokinetics of inhaled iloprost, aerosolized by three different devices, in severe pulmonary hypertension," Chest 124, 1294-1304 (2003).
Ozyazgan, Irfan M, Melli M, et al. Eicosanoids and inflammatory cells in frostbitten tissue: prostacyclin, thromboxane, polymorphonuclear leukocytes, and mast cells. Plast Reconstr Surg 1998;101(7): 1881-6.
Page, M.J., et al., "The PRISMA 2020 statement: an updated guideline for reporting systematic reviews," pp. 1-9 (2020).
Pandey et a., "Case Report. Severe Frostbite in Extreme Altitude Climbers—The Kathmandu Iloprost Experience," Wilderness & environmental medicine 29:366-374 (2018).
Patel et al., "Intra-arterial Thrombolysis for Extremity Frostbite Decreases Digital Amputation Rates and Hospital Length of Stay," Cardiovasc. Intervent. Radiol. 40:1824-1831 (2017).
Poole et al., "Management of severe frostbite with iloprost, alteplase and heparin," A Yukon case series. CMAJ open 9, E585-E591 (2021).
Poole et al., Treatment of severe frostbite with iloprost in northern Canada. CMAJ : Canadian Medical Association journal = journal de'lAssociation medicale canadienne 188:1255-1258 (2016).
Poole et al., Whitehorse frostbite protocol. https://yukon.ca/en/whitehorse-frostbite-protocol, 9 pages (revised 2020).
Pope et al., "Raynaud's phenomenon (primary)," BMJ Clin Evid. 2013; Oct. 10, 2013;2013:1119, 11 pages.
Rabl et al., "Long-term cyclic intravenous iloprost in systemic sclerosis: clinical experience from a single center," Reumatismo. 2012;64(3):158-165.

(56) References Cited

OTHER PUBLICATIONS

Rademaker et al., "Comparison of intravenous infusions of iloprost and oral nifedipine in treatment of Raynaud's phenomenon in patients with systemic sclerosis: a double blind randomised study," Br Med J. 298:561-564 (1989).

Rademaker et al., "Prolonged increase in digital blood flow following Iloprost infusion in patients with systemic sclerosis," Postgraduate Medical Journal 63:617-620 (1987).

Robson et al., "Evaluation of hand frostbite blister fluid as a clue to pathogenesis," The Journal of hand surgery 6, 43-47 (1981).

Rogers et al., The Effects of Rapid Rewarming on Tissue Salvage in Severe Frostbite Injury. Journal of burn care & research : official publication of the American Burn Association 43, 906-911 (2022).

Rotondo et al., "Evidence for increase in finger blood flow, evaluated by laser Doppler flowmetry, following iloprost infusion in patients with systemic sclerosis. A week-long observational longitudinal study," Scandinavian journal of rheumatology 47:311-318 (2018).

Ruan et al., "Prostacyclin therapy for pulmonary arterial hypertension," Texas Heart Institute journal 37:391-399 (2010).

Sadler et al., "Recruitment of hard-to-reach population subgroups via adaptations of the snowball sampling strategy," Nurs Health Sci. 2010;12(3):369-374.

Saemi et al., "Treatment of bilateral hand frostbite using transcatheter arterial thrombolysis after papaverine infusion," Cardiovasc Intervent Radiol. 32(6):1280-3. (Nov. 2009)/ Epub May 16, 2009.

Salimi et al., "Assessment of tissue viability in frostbite by 99mTc Pertechnetate Scintigraphy," AJR Am J Roentgenol 142:415-419 (1984).

Salimi et al., "Treatment of frostbite with i.v.streptokinase: an experimental study in rabbits," AJR Am J Roentgenol. 1987;149:773-776.

Sanchez et al., Immunosuppressive therapy in connective tissue diseases-associated pulmonary arterial hypertension. Chest. 2006; 130(1):182-189.

Schioppo et al., "Acute and chronic effects of two different intravenous iloprost regimens in systemic sclerosis. A pragmatic non-randomized trial," Rheumatology (Oxford, England) 57, 1408-1416 (2018).

Schror et al., "The antiplatelet and cardiovascular actions of a new carbacyclin derivative (ZK 36 374)—equipotent to PGI2 in vitro," Naunyn Schmiedebergs Arch. Pharmacol. 316, 252-255 (1981).

Scorza et al., "Effects of long-term cyclic iloprost therapy in systemic sclerosis with Raynaud's phenomenon. A randomized, controlled study," Clinical and experimental rheumatology 19, 503-508 (2001).

Sears et al., "Economic analysis of revision amputation and replantation treatment of finger amputation injuries," Plastic and recconstructive surgery 133: 827-840 (2014).

Shenaq et al., "Urban Frostbite. Strategies for Limb Salvage," Journal of burn care & research : official publication of the American Burn Association 40:613-619 (2019).

Silva et al. "Endothelial Dysfunction and Nailfold Videocapillaroscopy Pattern as Predictors of Digital Ulcers in Systemic Sclerosis: a Cohort Study and Review of the Literature," Clin Rev Allergy Immunol. Oct. 2015;49(2):240-52.

Steen et al., "Digital ulcers: overt vascular disease in systemic sclerosis," Rheumatology (Oxford). Jun. 2009;48 Suppl 3:iI119-24.

Steinberg et al., "Effect of a prostacyclin derivative (iloprost) on regional blood flow, sympathetic nerve activity, and baroreceptor reflex in the conscious rat," J Cardiovasc Pharmacol 11, 84-89 (1988).

Sunderkotter et al, "Pathophysiology and clinical consequences of Raynaud's phenomenon related to systemic sclerosis," Rheumatology (Oxford). 2006;45 Suppl 3:iI133-35.

Taylor et al., Frostbite injuries during winter maneuvers. A long-term disability. Mil.Med 154:411-412 (1989).

Thompson, "Why sources of heterogeneity in meta-analysis should be investigated," BMJ. 1994;309(6965):1351-1355.

Torley et al., "A double blind, randomised, multicentre comparison of two doses of intravenous iloprost in the treatment of Raynaud's phenomenon secondary to connective tissue diseases," Ann Rheum Dis. 1991;50(11):800-804.

Tremoli et al., "Mode of action of PGI2 and of its stable derivative iloprost on platelets and leukocytes," Throm Res Suppl. 1990;11:33-42.

Trombetta et al., "Effects of Longterm Treatment with Bosentan and Iloprost on Nailfold Absolute Capillary Number, Fingertip Blood Perfusion, and Clinical Status in Systemic Sclerosis," The Journal of rheumatology 43, 2033-2041 (2016).

Tsai et al., "Interaction between platelet receptor and iloprost isomers," Biochim.Biophys.Acta 942, 220-226 (1988).

Tsou et al., "Scleroderma dermal microvascular endothelial cells exhibit defective response to pro-angiogenic chemokines," Rheumatology (Oxford). 2016;55(4):745- 754.

Twomey et al., An open-label study to evaluate the safety and efficacy of tissue plasminogen activator in treatment of severe frostbite. The Journal of trauma 59, 1350-4; discussion 1354-1355 (2005).

Van Den Hoogen et al., "Classification Criteria for Systemic Sclerosis: An ACR-Eular Collaborative Initiative," Arthritis Rheum. Nov. 2013; 65(11): 2737-2747. Published online Oct. 3, 2013.

Viechtbauer, "Conducting Meta-Analyses inRwith themetaforPackage," Journal of Statistical Software. 2010;36(3):48.

Viswanath et al., "Systemic sclerosis: current concepts in pathogenesis and therapeutic aspects of dermatological manifestations," Indian J Dermatol. 2013;58(4):255-268.

Walker et al., "Clinical risk assessment of organ manifestations in systemic sclerosis: a report from the EULAR Scleroderma Trials And Research group database," Ann Rheum Dis. Jun. 2007;66(6):754-763. Epub Jan. 18, 2007.

Watson et al., "Seasonal variation of Raynaud's phenomenon secondary to systemic sclerosis.," J Rheumatol. 26:1734-1737 (1999).

Wexler et al., "The Use of Thrombolytic Therapy in the Treatment of Frostbite Injury," J Burn Care Res. 2017;38(5):e877-e881.

Wigley, "Clinical practice," Raynaud's phenomenon. N Engl J Med. 2002;347(13):1001-1008.

Wigley et al., "Intravenous Iloprost Treatment of Raynaud's Phenomenon and Ischemic Ulcers Secondary to Systemic Sclerosis," J. Rheumatol 19:1407-1414 (1992).

Wigley et al., "Raynaud's Phenomenon," N Engl J Med 375, 556-565 (2016).

Wigley F.M., et al., "Intravenous Iloprost Infusion in Patients with Raynaud Phenomenon Secondary to Systemic Sclerosis," Annals of Internal Medicine, Feb. 1994, vol. 120(3), pp. 199-206.

Wigley, "Raynaud's phenomenon and other features of scleroderma, including pulmonary hypertension," Curr Opin Rheumatol. 1996;8(6):561-568.

Wong et al., "Dynamic bone imaging with 99mTc-labeled diphosphonates and 18F-NaF. Mechanisms and applications," Journal of nuclear medicine: official publication, Society of Nuclear Medicine 54: 590-599 (2013).

Woo et al.., Proposed treatment protocol for frostbite. A retrospective analysis of 17 cases based on a 3-year single-institution experience. Arch. Plast. Surg. 40, 510-516 (2013).

Yardumian et al., "Platelet hyperaggregability occurring during prolonged continuous intravenous infusions of prostacyclin analogue ZK 36374," British journal of haematology 60:109-116 (1985).

Yardumian et al., "Successful treatment of Raynaud's syndrome with Iloprost, a chemically stable prostacyclin analogue," Br J Rheumatol 27: 220-226 (1988).

Yigit, "Review of our 10 years experience in cold burns at the burn center in the Southeast Anatolia region of Turkey," Ulus Travma Acil Cerrahi Derg. 2022;28(3):369-374.

Young et al., "Hand Impairment in Systemic Sclerosis: Various Manifestations and Currently Available Treatment," Current Treatment Options in Rheumatology vol. 2, pp. 252-269 (2016).

Zachariae et al., "Treatment of ischaemic digital ulcers and prevention of gangrene wit intravenous iloprost in systemic sclerosis," Acta Derm Venereol. 1996;76(3):236-238 (1996).

(56) References Cited

OTHER PUBLICATIONS

Zhang et al., "Management and Outcome of Feet Deep Frostbite Injury ( II and IV Degrees): A Series Report of 36 Cases," Int J Low Extrem Wounds. 2022;21(3):325-331.
Zhao et al., "Deep frostbite. Clinical characteristics and outcomes in northeastern China," Journal of tissue viability 29:110-115 (2020).
Zhu et al., "A prostacyclin analogue, iloprost, protects from bleomycin-induced pulmonary fibrosis in mice," Respir Res. 11:34, 12 pages (2010).
Gauthier et al., Iloprost for the treatment of frostbite: a scoping review, Int Journal Circumpolar Health vol. 82, 2189552, pp. 1-15 (Mar. 26, 2023).
International Search Report and Written Opinion for PCT Application No. PCT/US2024/038455 mailed Sep. 10, 2024 10 pages.
Jin et al., Expert consensus on the prevention, diagnosis and treatment of cold injury in china, 2020, Military Medical Researc 8(6), pp. 1-13 (Jan. 21, 2021).
Maundrell et al., "Epidemiology of Raynaud's Phenomenon", Wigley et al. eds., Raynaud's Phenomenon: A Guide to Pathogenesis and Treatment, 2015, pp. 21-35.
Metcalfe, "Microbiological Quality of Drug Products after Penetration of the Container System for Dose Preparation Prior to Patient Administration", American Pharmaceutical Review, 2009, 7 pages.
Gomez-Broughton, "Aseptic Processing of Biological Products: Current Regulatory Issues", Aug. 2018, CDER Microbiology Issues: A Deeper Dive, 33 pages.
The World Health Organization guidance on the subject: WHO Technical Report Series, No. 863, Thirty-fourth Report, 1996, Annex 5—Guidelines for stability testing of pharmaceutical products containing well established drug substances in conventional dosage forms, pp. 65-79.
Gibaldi et al., "Pharmacokinetics", 2nd ed. New York: Marcel Dekker, Inc., 1982, Chapter 11, pp. 408-417.

METHOD OF USING ILOPROST FOR TREATING FROSTBITE

CROSS-REFERENCE TO RELATED APPLICATIONS

This application claims the benefit of U.S. Provisional Application No. 63/514,244, filed Jul. 18, 2023, the disclosures of which are incorporated by reference herein in its entirety.

FIELD OF THE INVENTION

The present disclosure generally relates to treatment of frostbite by intravenous injection or intravenous infusion of iloprost or a pharmaceutically acceptable salt thereof.

BACKGROUND OF THE INVENTION

Frostbite is a thermal injury caused when tissue is exposed to freezing temperatures long enough for ice crystals to form in the affected tissue. The overall incidence of frostbite injury in the United States (US) is extremely low at 0.83 cases per year per 100,000 people. In addition, as the majority of cases are for superficial frostbite (64.8%) compared to severe frostbite injury (35.2%), severe (grade 3 and grade 4) frostbite is a very rare condition estimated at <1,000 cases annually in the US (Endorf et al., *J. Burn Care Res.* 2022, 43 (3), 646-651).

Iloprost is a stable synthetic analogue of prostacyclin (prostaglandin I$_2$; [PGI2]), which exerts anti-platelet activity and reverses vasoconstriction within peripheral and systemic arterial vascular beds (Ruan et al., *Tex. Heart Inst. J.* 2010, 37 (4), 391-399; Majed et al., *Pharmacol Rev.* 2012, 64 (3), 540-582). Iloprost infusion is associated with immediate generalized vasodilation, with the ratio of antiaggregatory:vasodilatory potency in vivo on the order of 2-7:1 (Schrör et al., *Naunyn Schmiedebergs Arch. Pharmacol.* 1981, 316 (3), 252-255; Hermán et al., *Arch. Int. Pharmacodyn. Ther.* 1989, 300, 281-291).

Severe frostbites commonly result in amputation of the affected extremity. Traumatic digit amputations, such as amputations due to frostbite, are detrimental to the activities of daily living and work (Boulas, H. J., *J. Am. Acad. Orthop. Surg.* 1998, 6, 100-105; Sears et al., *Plast. Reconstr. Surg.* 2014, 133, 827-840). Furthermore, because the hands are so visible, digit amputation can lead to social withdrawal and reduced quality of life (Hannah, S. D. *J. Hand Ther.* 2011, 24 (2), 95-102). Thus, there is a need for an effective therapy to treat severe frostbite to prevent or reduce the risks of digit amputations.

SUMMARY OF THE INVENTION

The present disclosure provides methods of treating frostbite in a subject, comprising administering a composition comprising iloprost or a pharmaceutically acceptable salt thereof at a concentration in the range of about 0.8 mcg iloprost or a pharmaceutically acceptable salt thereof per 1 mL of pharmaceutically acceptable carrier (about 0.8 mcg/mL) to about 1.1 mcg/mL.

In one embodiment of the method as disclosed herein, the composition comprising iloprost or a pharmaceutically acceptable salt thereof has a concentration of about 0.9 mcg/mL. In some embodiments, the composition comprising iloprost or a pharmaceutically acceptable salt thereof has a concentration of about 1 mcg/mL.

In one embodiment of the method as disclosed herein, the administering is by intravenous injection or intravenous infusion. In some embodiments, the administering is by continuous infusion.

In one embodiment of the method as disclosed herein, the administering is at one or more doses between about 0.2 ng/kg/min and about 3.0 ng/kg/min. In some embodiments, the administering is at one or more doses between about 0.25 ng/kg/min and about 2.0 ng/kg/min.

In one embodiment of the method as disclosed herein, the administering comprises a titration step on a first day of administration. In some embodiments, the administering comprises the titration step on a second day of administration. In some embodiments, the administering comprises the titration step on a third day of administration.

In one embodiment of the method as disclosed herein, the titration step comprises administering the composition at a starting dose of about 0.25 ng/kg/min, about 0.3 ng/kg/min, about 0.4 ng/kg/min, about 0.5 ng/kg/min, about 0.6 ng/kg/min, or about 0.7 ng/kg/min.

In one embodiment of the method as disclosed herein, the titration step comprises administering the composition at the starting dose of about 0.5 ng/kg/min. In some embodiments, the subject does not have a pre-existing Child-Pugh Class B or Child-Pugh Class C hepatic impairment.

In one embodiment of the method as disclosed herein, the dose is decreased to about 0.25 ng/kg/min at the beginning of the titration step when the subject has a renal impairment with eGFR less than 30 mL/min/m$^2$ and the subject cannot tolerate the starting dose of about 0.5 ng/kg/min.

In one embodiment of the method as disclosed herein, the titration step comprises administering the composition at the starting dose of about 0.25 ng/kg/min. In some embodiments, the subject has a Child-Pugh Class B or Child-Pugh Class C hepatic impairment.

In one embodiment of the method as disclosed herein, the titration step comprises increasing the dose every 10 minutes, 15 minutes, 20 minutes, 25 minutes, 30 minutes, 35 minutes, 40 minutes, 45 minutes, 50 minutes, 55 minutes, or 60 minutes until a maximum dose is reached. In some embodiments, the dose is increased every 30 minutes.

In one embodiment of the method as disclosed herein, the titration step comprises increasing the dose in increments of about 0.1 ng/kg/min, about 0.2 ng/kg/min, about 0.25 ng/kg/min, about 0.3 ng/kg/min, about 0.4 ng/kg/min, about 0.5 ng/kg/min, about 0.6 ng/kg/min, about 0.7 ng/kg/min, or about 0.8 ng/kg/min until a maximum dose is reached. In some embodiments, the dose is increased in increments of about 0.5 ng/kg/min. In some embodiments, the dose is increased in increments of about 0.25 ng/kg/min.

In one embodiment of the method as disclosed herein, the maximum dose is predetermined. In some embodiments, the predetermined maximum dose is about 1.8 ng/kg/min, about 2.0 ng/kg/min, about 2.2 ng/kg/min, about 2.4 ng/kg/min, about 2.6 ng/kg/min, about 2.8 ng/kg/min, or about 3.0 ng/kg/min. In some embodiments, the predetermined maximum dose is about 2.0 ng/kg/min.

In one embodiment of the method as disclosed herein, the maximum dose is about 2.0 ng/kg/min or the highest dose the subject can tolerate between 0.25 ng/kg/min and 2.0 ng/kg/min. In some embodiments, the maximum dose is about 2.0 ng/kg/min or the highest dose the subject can tolerate between 0.5 ng/kg/min and 2.0 ng/kg/min.

In one embodiment of the method as disclosed herein, the titration step comprises decrease in the dose if the subject has a dose-limiting reaction. In some embodiments, the dose-limiting reaction is headache, flushing, jaw pain, myalgia, nausea, or vomiting. In some embodiments, the dose is decreased in increments of about 0.5 ng/kg/min every 30 minutes until a tolerated dose is reached.

In one embodiment of the method as disclosed herein, the composition is administered continuously each day during a treatment period. In some embodiments, the continuous administration per day is about 4 hours, about 5 hours, about 6 hours, about 7 hours, or about 8 hours. In some embodiments, the continuous administration per day is about 6 hours. In some embodiments, the treatment period comprises the titration step on the first day, the second day, and/or the third day.

In one embodiment of the method as disclosed herein, once the maximum dose is determined in the titration step, the maximum dose is maintained for the remainder of the treatment period.

In one embodiment of the method as disclosed herein, the composition is administered for 4, 5, 6, 7, 8, 9, or 10 consecutive days. In some embodiments, the composition is administered for a maximum of 8 consecutive days.

In one embodiment of the method as disclosed herein, the administering is at the maximum dose found in the titration step (titration step performed on day 1, day 2, or day 3) on a fourth day and beyond.

In one embodiment of the method as disclosed herein, the administering is stopped if the subject has a dose-limiting reaction before the treatment period is over. In some embodiments, the administering is re-initiated at a previously tolerated dose after the subject's dose-limiting reaction is resolved.

In one embodiment of the method as disclosed herein, the pharmaceutically acceptable carrier is an IV fluid. In some embodiments, the pharmaceutically acceptable carrier is 0.9% sodium chloride solution, 0.45% sodium chloride solution, 0.33% sodium chloride solution, 0.225% sodium chloride solution, 5% dextrose in water (D5W), 2.5% dextrose in water (D2.5W), 5% dextrose in lactated Ringer's solution (D5LRS), Ringer's solution (RS), or sterile water. In some embodiments, the pharmaceutically acceptable carrier is 0.9% sodium chloride solution.

In one embodiment of the method as disclosed herein, the method further comprises diluting 100 mcg/mL iloprost or pharmaceutically acceptable salt thereof concentrated solution using sodium chloride solution to provide iloprost or pharmaceutically acceptable salt thereof composition with a concentration in the range of about 0.8 mcg/mL to about 1.1 mcg/mL. In some embodiments, 1 mL of the 100 mcg/mL iloprost or pharmaceutically acceptable salt thereof concentrated solution is in a single dose vial. In some embodiments, the single dose vial is a glass vial.

In one embodiment of the method as disclosed herein, the most common adverse event is headache, flushing, palpitations/tachycardia, nausea, vomiting, dizziness, or hypotension.

In one embodiment of the method as disclosed herein, safety profile of the method in the subject is consistent with safety profile observed in systemic sclerosis subjects experiencing symptomatic digital ischemic episodes from multicenter, double-blind, randomized, placebo-controlled studies with iloprost continuous infusion.

In one embodiment of the method as disclosed herein, the frostbite is a stage 3 or a stage 4 frostbite. In some embodiments, the frostbite is a severe frostbite.

In one embodiment of the method as disclosed herein, the method prevents or reduces the risk of digit amputation.

DETAILED DESCRIPTION

Figure 1:
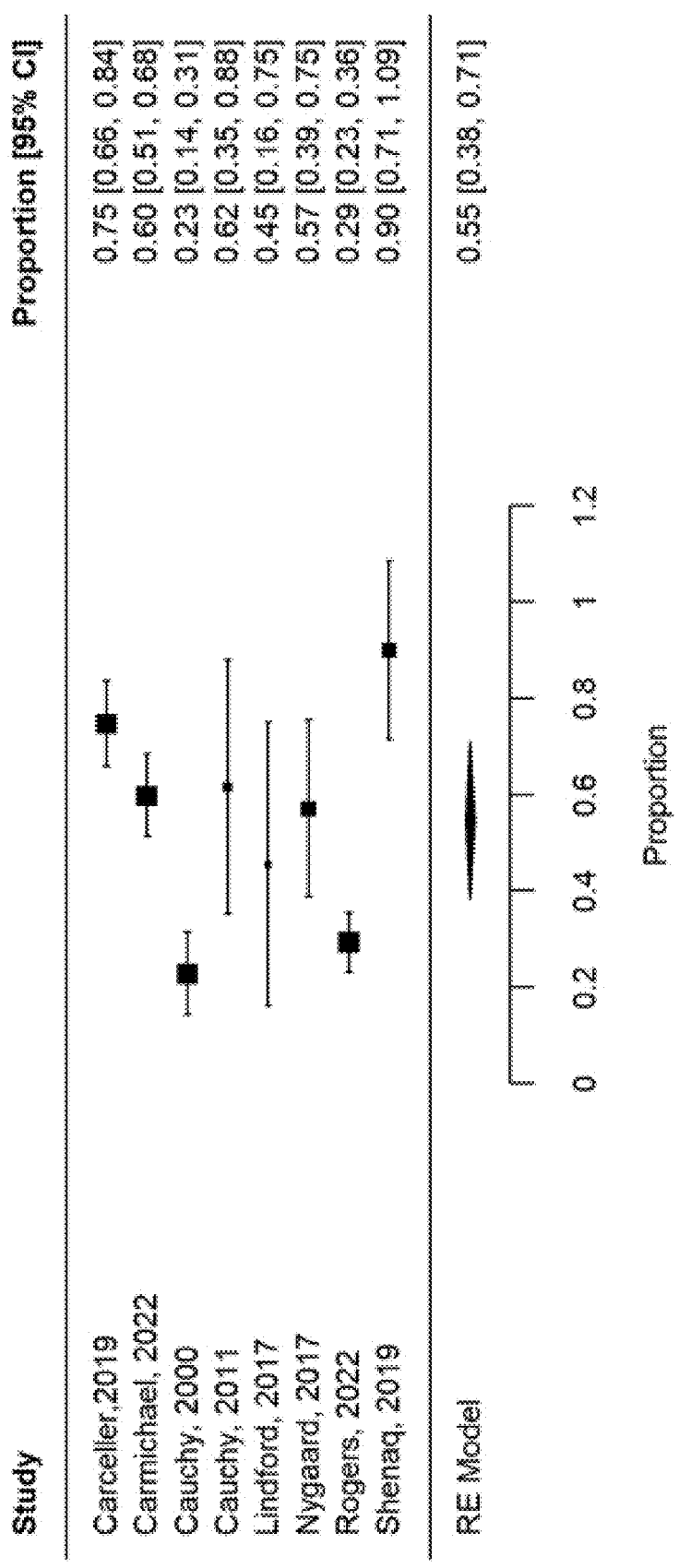
FIG. 1 shows proportion of patients with amputation after standard of care treatment for frostbite.

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a therapeutic agent" refers to one or more therapeutic agents or at least one therapeutic agent. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable salts" includes both acid and base addition salts. Pharmaceutically acceptable salts include those obtained by reacting the active compound functioning as an acid, with an inorganic or organic base to form a salt. Organic base includes, but are not limited to, monoethanolamine, diethanolamine, triethanolamine, trometamol and meglumine. Those skilled in the art will further recognize that base addition salts may be prepared by reaction of the compounds with the appropriate inorganic or organic base via any of a number of known methods.

The term "treating" means one or more of relieving, alleviating, delaying, reducing, improving, or managing at least one symptom of a condition in a subject. The term "treating" may also mean one or more of arresting, delaying the onset (i.e., the period prior to clinical manifestation of the condition) or reducing the risk of developing or worsening a condition.

The compound of the invention, or their pharmaceutically acceptable salts contain asymmetric centers and can thus give rise to enantiomers, diastereomers, and other stereoisomeric forms that can be defined, in terms of absolute stereochemistry, as (R) or (S). The present disclosure is meant to include all such possible isomers, as well as their racemic and optically pure forms whether or not they are specifically depicted herein. Stereoisomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). The compound described herein also contains an olefinic double bond, and unless specified otherwise, it is intended that the compounds include both E and Z geometric isomers.

A "stereoisomer" refers to a compound made up of the same atoms bonded by the same bonds but having different three-dimensional structures, which are not interchangeable. The present disclosure contemplates various stereoisomers and mixtures thereof and includes diastereomers.

Pharmaceutically Active Ingredient

The present disclosure relates to use of iloprost or a pharmaceutically acceptable salt thereof or a stereoisomer thereof for treating frostbite. Iloprost has the following structure and can also be identified as (5E)-5-[(3aS,4R,5R, 6aS)-5-hydroxy-4-[(E,3S)-3-hydroxy-4-methyloct-1-en-6-ynyl]-3,3a,4,5,6,6a-hexahydro-1H-pentalen-2-ylidene]pentanoic acid.

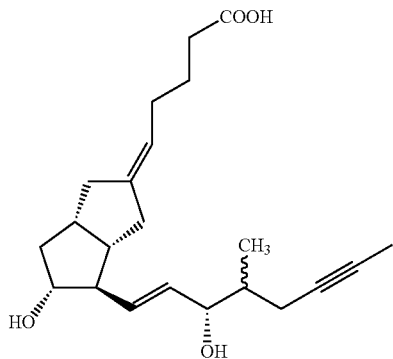 [SMILES: CC#CCC(C)[C@H](O)/C=C/[C@@H]1[C@H]2C/C(=C/CCCC(=O)O)C[C@H]2C[C@H]1O]

In some embodiment, iloprost consists of a mixture of the 4R and 4S diastereomers. In some embodiments, iloprost consists of a mixture of the 4R and 4S diastereomers at a ratio of about 1:1. In some embodiments, iloprost consists of a mixture of the 4R and 4S diastereomers at a ratio of about 53:47.

The present disclosure also relates to pharmaceutical composition comprising iloprost or a pharmaceutically acceptable salt thereof or a stereoisomer thereof.

International Application Publication Nos. WO222/032141 and WO2022/036234 disclosed iloprost composition and treatment, each of which is hereby incorporated by reference in its entirety for all purposes.

Iloprost Composition

The present disclosure relates to administering a composition comprising iloprost or a pharmaceutically acceptable salt or a stereoisomer thereof. In some embodiment, the composition is a pharmaceutical composition.

In some embodiments, iloprost or a pharmaceutically acceptable salt or a stereoisomer thereof, is formulated for injection. In some embodiments, iloprost or a pharmaceutically acceptable salt or a stereoisomer thereof, is formulated for intravenous injection or intravenous infusion. In some embodiments, iloprost or a pharmaceutically acceptable salt or a stereoisomer thereof, is formulated for continuous infusion.

In embodiments, iloprost, or a pharmaceutically acceptable salt or a stereoisomer thereof, is formulated as a sterile solution. In embodiments, a composition comprising iloprost or a pharmaceutically acceptable salt or a stereoisomer thereof, further comprises a pharmaceutically acceptable carrier or excipient.

Pharmaceutically acceptable excipients include, but are not limited to, solubilizing agents, pH adjusting agents, tonicity agents, buffering agents, and/or solvents.

In embodiments, solubilizing agents is selected from pharmaceutically acceptable alcohols, glycols, esters, ethers, or silicones. In embodiments, the solubilizing agent is ethanol.

In embodiments, pH adjusting agents is a pharmaceutically acceptable acid or base. In embodiments, the pH adjusting agent is hydrochloric acid.

In embodiments, tonicity agents include, but are not limited to, glycerin, lactose, mannitol, dextrose, sodium chloride, sodium sulfate, and sorbitol. In embodiments, the tonicity agent is sodium chloride.

In embodiments, buffering agents include, but not limited to, citrate buffer, phosphate buffer, phosphate citrate buffer, bicarbonate buffer, tartrate buffer, acetate buffer, and trometamol buffer. In embodiments, the buffering agent is trometamol.

In embodiments, solvents are sterile solvents. In some embodiments, the sterile solvent is an IV fluid. In embodiments, solvents include, but are not limited to, water, glucose solution, dextrose solution, saline solution, Ringer's solution, and lactated Ringer's solution. In some embodiments, saline solution is 0.9% sodium chloride solution, 0.45% sodium chloride solution, 0.33% sodium chloride solution, or 0.225% sodium chloride solution. In some embodiments, dextrose solution is 5% dextrose in water (D5W), 2.5% dextrose in water (D2.5W) or 5% dextrose in lactated Ringer's solution (DSLRS). In embodiments, the solvent is water. In some embodiments, the solvent is 0.9% sodium chloride solution.

In embodiments, a composition comprising iloprost, or a pharmaceutically acceptable salt or a stereoisomer thereof, further comprises trometamol, ethanol, sodium chloride, hydrochloric acid, and water.

In embodiments, a composition comprising iloprost, or a pharmaceutically acceptable salt or a stereoisomer thereof, contains no preservatives.

In embodiments, a composition comprising iloprost, or a pharmaceutically acceptable salt or a stereoisomer thereof, is provided as a single use vial. In embodiments, a composition comprising iloprost, or a pharmaceutically acceptable salt or a stereoisomer thereof, is provided as a single dose vial. In some embodiments, the single use vial or the single dose vial is a glass vial. In embodiments, each vial comprises about 100 mg iloprost. In embodiments, each vial comprises about 100 mcg iloprost per 1 mL of pharmaceutically acceptable carrier and/or excipients. In embodiments, each single use vial or single dose vial has composition comprising about 100 mcg iloprost or a pharmaceutically acceptable salt or a stereoisomer thereof. In embodiments, each single use vial or single dose vial has a composition comprising about 100 mcg (0.1 mg) iloprost or a pharmaceutically acceptable salt or a stereoisomer thereof, about 8.1 mg ethanol, about 0.242 mg tromethamine, and about 0.9 mg sodium chloride. In embodiments, each single use vial or single dose vial has a pH of about 8.3. In embodiments, each single use vial or single dose vial has a pH of about 8.3 which is adjusted with hydrochloric acid and sodium hydroxide. In embodiments, each single use vial or single dose vial has a volume of 1 mL which is filled with water for injection to make 1 mL after above-described ingredients are measured.

A glass vial comprising 100 mcg iloprost per 1 mL of pharmaceutically acceptable carrier and/or excipients provides an important advancement in the pharmaceutical use of iloprost.

Before approval of AURLUMYN™, all approved iloprost was sold in glass ampules around the world. Glass ampules are associated with safety risks including percutaneous injuries to healthcare professionals when breaking glass ampules and accidental transfer of glass particulate matter during pharmacy compounding. Accidental transfer of glass particulate, which could be a result of health professional not using an appropriate filter needle when transferring the ampule contents, is especially dangerous as it can result in the injection of glass particles to patients and cause serious adverse events. Adverse events associated with accidental injection of glass particulates include pulmonary thrombi, micro-emboli, infusion phlebitis, end-organ granuloma formation and inflammation. These risks associated with the use of glass ampules can be eliminated by providing the therapeutics in a glass vial. In addition, a single use vial would further reduce potential mistakes in diluting the therapeutics for infusion compared to needing to combine the contents of two or more drug preparations (ampule or vial) or syringing out a set amount from an appropriate vessel containing larger quantities of the therapeutics.

In embodiments, the single use or the single dose vial containing iloprost is stored at room temperature (20° C. to 25° C.). In embodiments, the single use or the single dose vial containing iloprost is stored at a temperature between about 20° C. to about 25° C. with allowed temperature excursions permitted to 15° C. to 30° C. In embodiments, the single use or the single dose vial containing iloprost is stored at a temperature between about 20° C. to about 25° C. In embodiments, the single use or the single dose vial containing iloprost is stored at a refrigerated temperature (approximately 5° C.). In embodiments, the single use or the single dose vial containing iloprost is protected from light when stored. In embodiments, the single use or the single dose vial contains 100 μg iloprost per 1 mL.

In embodiments, the single use or the single dose vial containing iloprost is stable at 25° C. for at least 6 months. In embodiments, the single use or the single dose vial containing iloprost is stable at 25° C. for at least 12 months. In embodiments, the single use or the single dose vial containing iloprost is stable at 25° C. for at least 18 months.

In embodiments, the single use or the single dose vial containing iloprost is stable at 25° C. and at 60% relative humidity (RH) for at least 6 months. In embodiments, the single use or the single dose vial containing iloprost is stable at 25° C./60% RH for at least 12 months. In embodiments, the single use or the single dose vial containing iloprost is stable at 25° C./60% RH for at least 18 months.

In embodiments, the single use or the single dose vial containing iloprost is stable at 40° C. for at least 1 months. In embodiments, the single use or the single dose vial containing iloprost is stable at 40° C. for at least 3 months. In embodiments, the single use or the single dose vial containing iloprost is stable at 40° C. for at least 6 months.

In embodiments, the single use or the single dose vial containing iloprost is stable at 40° C. and at 75% relative humidity (RH) for at least 1 months. In embodiments, the single use or the single dose vial containing iloprost is stable at 40° C./75% RH for at least 3 months. In embodiments, the single use or the single dose vial containing iloprost is stable at 40° C./75% RH for at least 6 months.

In embodiments, the single use or the single dose vial containing iloprost is stable at 5° C. for at least 3 months. In embodiments, the single use or the single dose vial containing iloprost is stable at 5° C. for at least 6 months. In embodiments, the single use or the single dose vial containing iloprost is stable at 5° C. for at least 9 months.

In embodiments, a composition comprising iloprost, or a pharmaceutically acceptable salt or a stereoisomer thereof, has a pH of about 7.0 to about 9.0. In embodiments, a composition comprising iloprost, or a pharmaceutically acceptable salt or a stereoisomer thereof, has a pH of about 8.0 to about 9.0.

In embodiments, a composition comprising iloprost, or a pharmaceutically acceptable salt or a stereoisomer thereof, is further diluted with a sterile solvent for injection or infusion. In embodiments, the composition is further diluted with 0.9% sodium chloride solution, 0.45% sodium chloride solution, 0.33% sodium chloride solution, 0.225% sodium chloride solution, 5% dextrose in water (D5W), 2.5% dextrose in water (D2.5W), 5% dextrose in lactated Ringer's solution (D5LRS), Ringer's solution (RS), or sterile water. In embodiments, the composition is further diluted with saline solution for injection or infusion. In some embodiments, the composition is further diluted with 0.9% sodium chloride solution. In embodiments, the composition is further diluted with 0.9% sodium chloride injection, USP.

In embodiments, a composition comprising iloprost, or a pharmaceutically acceptable salt or a stereoisomer thereof, for injection or infusion is at a concentration in the range of about 0.8 mcg iloprost or a pharmaceutically acceptable salt thereof per 1 mL of pharmaceutically acceptable carrier (0.8 mcg/mL) to about 1.1 mcg/mL. In some embodiments, the composition or the composition has a concentration of about 0.9 mcg/mL. In some embodiments, the composition or the composition has a concentration of about 1 mcg/mL (1,000 ng/mL).

In embodiments, 1 mL of the composition comprising 100 mcg of iloprost or pharmaceutically acceptable salt thereof per 1 mL is diluted with 99 mL of 0.9% sodium chloride. In embodiments, 1 mL of 100 mcg iloprost/mL is diluted with 99 mL of 0.9% sodium chloride injection, USP, to provide iloprost concentration of 1,000 ng/ml (1 mcg/mL).

In embodiments, 1 mL of the composition comprising 100 mcg of iloprost or pharmaceutically acceptable salt thereof per 1 mL is added to an infusion bag labeled to contain 100 mL 0.9% sodium chloride injection, USP, without concern for overfill. In embodiments, 1 mL of 100 mcg iloprost/mL is diluted with 0.9% sodium chloride injection, USP, to provide iloprost concentration between about 0.8 mcg/mL and about 1.1 mcg/mL.

In embodiments, diluted composition is ready to use and can be used immediately, or stored at refrigerated temperatures (2° C. to 8° C.) for a maximum of 8 days prior to use, or stored at room temperature (20° C. to 25° C.) for 4 hours prior to administration as a 6-hour continuous infusion. In embodiments, continuous infusion is continuous intravenous infusion.

In embodiments, a composition comprising iloprost, or a pharmaceutically acceptable salt or a stereoisomer thereof, for injection or infusion is at a concentration of about 25 µg Iloprost per 1 mL. In embodiments, 25 µg Iloprost per 1 mL composition is ready to use and can be used immediately, or stored at refrigerated temperatures (2° C. to 8° C.) for a maximum of 8 days prior to use, or stored at room temperature (20° C. to 25° C.) for 4 hours prior to administration as a 6-hour continuous infusion. In embodiments, continuous infusion is continuous subcutaneous infusion.

In embodiments, ready to use composition comprising iloprost or a pharmaceutically acceptable salt or a stereoisomer thereof, as disclosed herein is safe, efficacious, and stable for up to 8 days at 2° C. to 8° C. The 8-day stability for the ready to use composition is critical so that patients receive an accurate dose of iloprost or a pharmaceutically acceptable salt or a stereoisomer thereof and to minimize the risk of infection (sepsis or line-infection). In embodiments, the 8-day stability for the ready to use composition is important in enabling decentralized infusions in the patient's home setting or at an off-site ambulatory infusion sites, which reduces the patients' risk to nosocomial infections (contracting infection at a hospital or infusion center) and will improve patient convenience which reduces the risk of non-compliance.

In embodiments, a subcutaneous continuous infusion would use a more concentrated fully diluted ready to use iloprost product (e.g., 25 µg/mL instead of 1 µg/mL for intravenous infusion) but the dose delivered (ng/kg/min) and time of delivery (6 hours) would be equivalent.

Therapeutic Use

The present disclosure relates to administering iloprost or a pharmaceutically acceptable salt thereof or a stereoisomer thereof to a frostbite patient. In embodiments, the iloprost or a pharmaceutically acceptable salt thereof or a stereoisomer thereof is administered by injection. In embodiments, administration is by intravenous or subcutaneous injection. In embodiments, administration is by intravenous injection or intravenous infusion. In embodiments, administration is by continuous infusion. In embodiments, administration is by continuous infusion is intravenous infusion or subcutaneous infusion. In embodiments, administration is through peripheral catheter system, a peripheral inserted central catheter (PICC), or subcutaneous catheter in the abdomen. In embodiments, administration is through NovaCath Integrated IV Catheter System or a Poly Per-Q-Cath Catheter. In embodiments, the same peripheral catheter system or a peripheral inserted central catheter (PICC) is used for 1, 2, 3, 4, 5, 6, 7, or 8 days of treatment. In embodiments, the same peripheral catheter system or a peripheral inserted central catheter (PICC) is used during all consecutive days of treatment.

In embodiments of administering iloprost or a pharmaceutically acceptable salt thereof or a stereoisomer thereof to a frostbite patient, the administration is done at a medical facility by a medically trained professional. In embodiments, the administration is done at a decentralized setting. In embodiments, the administration is done at the subject's home or ambulatory infusion suite. In embodiments of the administration at a decentralized setting, the administration of iloprost or a pharmaceutically acceptable salt thereof or a stereoisomer thereof is performed by a medically trained professional. In embodiments of the administration at a decentralized setting, a physician is accessible by telehealth during the treatment to assess adverse events and vital signs.

In some embodiments, iloprost or a pharmaceutically acceptable salt thereof is administered to a subject at a concentration in the range of about 0.8 mcg iloprost or a pharmaceutically acceptable salt thereof per 1 mL of pharmaceutically acceptable carrier (about 0.8 mcg/mL) to about 1.1 mcg/mL. In some embodiments, iloprost or a pharmaceutically acceptable salt thereof is administered to a subject at a concentration of about 0.8 mcg/mL, about 0.9 mcg/mL, about 1.0 mcg/mL, or about 1.1 mcg/mL.

In some embodiments, concentrated solution of iloprost or a pharmaceutically acceptable salt thereof is diluted prior to therapeutic use. In some embodiments, the dilution is with a suitable IV fluid or suitable sterile injection solution. In some embodiments, the dilution is with 0.9% Sodium Chloride Injection, USP.

In some embodiments, 1 mL of the composition comprising 100 mcg of iloprost or pharmaceutically acceptable salt thereof per 1 mL is diluted with 99 mL of 0.9% sodium chloride solution. In embodiments, 1 mL of 100 mcg iloprost/mL is transferred into a 100 mL 0.9% sodium chloride solution infusion bag. In embodiments, 1 mL of 100 mcg iloprost/mL is transferred into a commercially available infusion bag labeled to contain 100 mL 0.9% sodium chloride solution (which contains overfill so the actual volume will be larger than 100 mL).

The present disclosure also relates to method for treatment of frostbite. In some embodiments, frostbite is severe frostbite. In some embodiments, frostbite is grade 3 or grade 4 frostbite.

In some embodiment, frostbite subject has at least one digit (finger or toe) affected by frostbite. In some embodiment, frostbite subject has at least one digit (finger or toe) with frostbite stage 3 (lesion extending just past the proximal phalanx) or stage 4 (lesion extending proximal to the metacarpal or metatarsal joint).

The present disclosure also relates to method for treatment of frostbite to reduce the risk of digit amputations.

The present disclosure also relates to administering iloprost or a pharmaceutically acceptable salt thereof or a stereoisomer thereof to a frostbite subject by intravenous injection, subcutaneous injection, intravenous infusion, or subcutaneous infusion. In embodiments, administration is by intravenous infusion or intravenous injection. In embodiments, administration is by continuous intravenous infusion.

In embodiments, an advantage of continuous infusion of iloprost or a pharmaceutically acceptable salt thereof or a stereoisomer thereof, is its greater bioavailability when compared to other routes of administration. For example, iloprost (a synthetic analog of prostacyclin, PGI2) has poor oral bioavailability and tolerability making oral administration route not viable.

In embodiments, another advantage of continuous infusion of iloprost or a pharmaceutically acceptable salt thereof or a stereoisomer thereof, is that the iloprost composition disclosed herein for infusion is stable which allows for home infusion and decentralized infusions.

In embodiments, another advantage of continuous infusion of iloprost or a pharmaceutically acceptable salt thereof or a stereoisomer thereof, is the ability for iloprost to act as a potent prostacyclin (IP-) receptor agonist. In embodiments, iloprost or a pharmaceutically acceptable salt thereof or a stereoisomer thereof, increases cyclic AMP concentrations in pertinent cells thereby having an effect as vasodilator or as an anti-vasoconstrictor, anti-fibrotic, anti-platelet, and/or anti-inflammatory. In embodiments, once iloprost or a pharmaceutically acceptable salt thereof or a stereoisomer thereof, reaches the site of action (digit cutaneous circulation), the infusion therapy would inhibit platelet aggregation.

As used herein, a treatment period refers to the duration to which a subject received iloprost or a pharmaceutically acceptable salt or stereoisomer thereof for the treatment for frostbite. In embodiments, iloprost or a pharmaceutically acceptable salt or stereoisomer thereof, is administered once a day for 3 to 10 consecutive days (i.e., the treatment period is 3 to 10 days). In embodiments, iloprost or a pharmaceutically acceptable salt or stereoisomer thereof, is administered once a day for 3 to 8 consecutive days. In embodiments, iloprost or a pharmaceutically acceptable salt or stereoisomer thereof, is administered once a day for up to 8 consecutive days.

In embodiments, iloprost or a pharmaceutically acceptable salt or stereoisomer thereof, is administered once a day via intravenous injection or infusion over about 4 hours to about 8 hours. In embodiments, iloprost or a pharmaceutically acceptable salt or stereoisomer thereof, is administered once a day via intravenous injection or infusion over about 4 hours, about 5 hours, about 6 hours, about 7 hours, or about 8 hours. In embodiments, iloprost or a pharmaceutically acceptable salt or stereoisomer thereof, is administered once a day via intravenous injection or infusion over about 6 hours.

In some embodiments, the administration is continuous, unless there is a need to pause the administration due to adverse events. In some embodiments, the continuous administration of iloprost or a pharmaceutically acceptable salt or stereoisomer thereof per day is for about 4 hours, about 5 hours, about 6 hours, about 7 hours, or about 8 hours. In some embodiments, the continuous administration of iloprost or a pharmaceutically acceptable salt or stereoisomer thereof per day is for about 6 hours. In some embodiments, the continuous administration of iloprost or a pharmaceutically acceptable salt or stereoisomer thereof per day is for about 6 hours and the treatment period is a maximum of 8 consecutive days. In some embodiments, the continuous administration is via intravenous injection or infusion.

In some embodiments, the continuous administration of iloprost or a pharmaceutically acceptable salt or stereoisomer thereof is once a day for about 4 hours, about 5 hours, about 6 hours, about 7 hours, or about 8 hours. In some embodiments, the continuous administration of iloprost or a pharmaceutically acceptable salt or stereoisomer thereof is once a day for about 6 hours. In some embodiments, the continuous administration of iloprost or a pharmaceutically acceptable salt or stereoisomer thereof is once a day for about 6 hours and the treatment period is a maximum of 8 consecutive days.

In some embodiments, iloprost or a pharmaceutically acceptable salt or stereoisomer thereof, is administered once a day via continuous infusion for 6 hours. In some embodiments, iloprost or a pharmaceutically acceptable salt or stereoisomer thereof, is administered once a day via continuous infusion for 6 hours for a maximum of 8 consecutive days.

In embodiments, iloprost or a pharmaceutically acceptable salt or stereoisomer thereof, is administered at a rate or a dose in the range of about 0.2 ng iloprost/kg body weight/min (ng/kg/min) to about 3.0 ng/kg/min. In embodiments, iloprost or a pharmaceutically acceptable salt or stereoisomer thereof, is administered at a rate or a dose in the range of about 0.25 ng/kg/min to about 2.0 ng/kg/min. In embodiments, the rate or the dose of injection or infusion is adjusted according to the subject's tolerability within the range of 0.25 to about 2.0 ng/kg/min. In embodiments, the rate or the dose of injection or infusion is adjusted according to the subject's tolerability within the range of 0.5 to about 2.0 ng/kg/min.

In embodiments, the administration rate or dose is titrated on the first day of treatment. In some embodiments, titration step is repeated on the second day of treatment. In some embodiments, titration step is repeated on the third day of treatment. In some embodiments, the treatment on the fourth day starts with the highest tolerated dose from the third day. During the iloprost treatment, the dose or the rate may be adjusted based on tolerability of the subject.

In embodiments, on the first day of treatment, administration of iloprost or a pharmaceutically acceptable salt or stereoisomer thereof, is initiated at a rate or a dose of about 0.25 ng/kg/min, about 0.3 ng/kg/min, about 0.4 ng/kg/min, about 0.5 ng/kg/min, about 0.6 ng/kg/min, or about 0.7 ng/kg/min (starting dose). In some embodiments, the starting dose is 0.5 ng/kg/min.

In some embodiments, the starting dose is 0.5 ng/kg/min if the subject does not have a pre-existing Child-Pugh Class B or Child-Pugh Class C hepatic impairment. In some embodiments, the starting dose is 0.5 ng/kg/min but the dose is decreased to about 0.25 ng/kg/min at the beginning of the titration step when the subject has a renal impairment with eGFR less than 30 mL/min/m2 and the subject cannot tolerate the starting dose of about 0.5 ng/kg/min.

In some embodiments, the starting dose is 0.25 ng/kg/min. In some embodiments, the starting dose is 0.25 ng/kg/min if the subject has a Child-Pugh Class B or Child-Pugh Class C hepatic impairment.

In embodiments, the rate or the dose of administration is increased stepwise during titration every 10 minutes, 15 minutes, 20 minutes, 25 minutes, 30 minutes, 35 minutes, 40 minutes, 45 minutes, 50 minutes, 55 minutes, or 60 minutes until a maximum dose is reached. In some embodiments, the rate or the dose of administration is increased stepwise during titration every 30 minutes until a maximum dose is reached.

In embodiments, the rate or the dose of administration is increased stepwise during titration in increments of about 0.1 ng/kg/min, about 0.2 ng/kg/min, about 0.25 ng/kg/min, about 0.3 ng/kg/min, about 0.4 ng/kg/min, about 0.5 ng/kg/min, about 0.6 ng/kg/min, about 0.7 ng/kg/min, or about 0.8 ng/kg/min until a maximum dose is reached. In some embodiments, the rate or the dose of administration is increased stepwise during titration in increments of about 0.5 ng/kg/min. In some embodiments, the rate or the dose of administration is increased stepwise during titration in increments of about 0.25 ng/kg/min.

In some embodiments, the maximum dose is predetermined. In some embodiments, the predetermined maximum dose is about 1.8 ng/kg/min, about 2.0 ng/kg/min, about 2.2 ng/kg/min, about 2.4 ng/kg/min, about 2.6 ng/kg/min, about 2.8 ng/kg/min, or about 3.0 ng/kg/min. In some embodiments, the predetermined maximum dose is about 2.0 ng/kg/min.

In some embodiments, the maximum dose is about 2.0 ng/kg/min or the highest dose the subject can tolerate between 0.25 ng/kg/min and 2.0 ng/kg/min.

In some embodiments, once the maximum dose is reached on a titration day (i.e., day 1, day 2, and/or day 3), the maximum dose is maintained for the remainder of the treatment for that day.

In embodiments, the rate or the dose of administration is increased about every 30 minutes in increments of 0.5 ng/kg/min up to 2.0 ng/kg/min to determine the maximum dose on the first day of the treatment. In embodiments, the second day and the third day of the treatment repeats the titration steps of the first day. In embodiments, the fourth day and thereafter is initiated at the maximum dose tolerated by the subject on treatment day 3. In embodiments, the rate or the dose of injection or infusion can be adjusted by the administering medical professional at any time during the treatment.

In some embodiments, the titration comprises decreasing in the dose if the subject has a dose-limiting reaction. In some embodiments, the dose-limiting reaction is headache, flushing, jaw pain, myalgia, nausea, or vomiting.

In some embodiments, the titration comprises decreasing in the dose if the subject has an adverse event. In some embodiments, the adverse event is headache, flushing, palpitations/tachycardia, nausea, vomiting, dizziness, or hypotension.

In embodiments, if the administration of iloprost or a pharmaceutically acceptable salt thereof or a stereoisomer thereof is stopped due to a dose-limiting adverse event, administration can be reinitiated at a previously tolerated rate or dose once the adverse event or the dose-limiting reaction is resolved.

In embodiments of administering iloprost or a pharmaceutically acceptable salt thereof or a stereoisomer thereof to a frostbite patient, the administration is temporarily interrupted if the patient experiences symptomatic hypotension, systolic blood pressure <80 mm HG, intolerable adverse events (e.g., vomiting), or a systolic blood pressure drop more than 10 mm Hg from the patient's pre-infusion measurement. In embodiments, when the patient's systolic blood pressure drops more than 10 mm Hg from the patient's pre-infusion measurement, a physician must determine if the infusion should be re-initiated after correcting the hypotension. In embodiments, symptomatic hypotension is any reduction of blood pressure associated with symptoms (e.g., dizziness, lightheadedness, syncope). In embodiments where the treatment is temporarily interrupted, a physician determines whether to re-initiate treatment after correcting hypotension.

In embodiments, iloprost or a pharmaceutically acceptable salt thereof or a stereoisomer thereof is administered to a frostbite subject through a peripheral line or peripherally inserted central catheter using an infusion pump. In embodiments of infusion administration, in-line 0.22 micron filter or 0.2 micron filter is used. In embodiments of infusion administration, infusion pump should be able to deliver rates between 0.1 to 99.99 mL per hour. In embodiments of infusion administration, infusion pump should be able to adjust infusion rates with increments of 0.1 mL per hour. In embodiments of infusion administration, infusion pump should be accurate to 5.0% of programmed rate. In embodiments of infusion administration, infusion pump should be positive pressure-driven (continuous or pulsatile). In embodiments, the reservoir or the infusion line set comprise polytetrafluoroethylene, fluorinated ethylenepropylene, polyvinylidene fluoride, polyether urethanes, polycarbonate urethanes, urethanes, polyurethanes, polyolefins, polyethylene, polypropylene, ethylene polymers, ethylene vinyl acetate, ethylene coacrylic acid, ethylene covinyl alcohol, polyimide, polyetheretherketone, polyaryletherketone, polysulfone, parylene, parylast, polyethlyene terephthalate, polyethylene oxide, silicones, polyesters; polyolefins, polyamides, polycaprolactams, polyvinyl chloride, polyacrylates, polymethacrylates; polyureas, polyvinylhalides, polyvinylidenehalides, polyvinylethers, polyvinylaromatics, polyvinylesters, alkyd resins, polysiloxanes, epoxy resins, polyvinyl methyl ether, polyvinyl alcohol, acrylic polymers and copolymers, polyacrylonitriles, polystyrene copolymers of vinyl monomers with olefins, styrene acrylonitrile copolymers, ethylene methyl methacrylate copolymers, ethylene vinyl acetate, polyethers, rayons, cellulosics, cellulose acetate; cellulose nitrate, cellulose propionate, or any derivatives, analogs, homologues, salts, copolymers or combinations thereof. In embodiments, the reservoir or the infusion line set can be made of polyvinyl chloride, polypropylene, silicone, ethyl vinyl acetate, copolyester ether, polyolefins, or the like, or combinations thereof. In embodiments, the reservoir and infusion line set can be made of polyvinyl chloride.

In embodiments, infusion rate of the dose when administering of about 1 mcg/mL iloprost or a pharmaceutically acceptable salt thereof (including about 0.8 mcg/mL to about 1.1 mcg/mL) can be calculated as follows:

$$\text{Infusion Rate (mL/}hr) = \frac{[\text{Dose (ng/kg/min)} \times \text{Weight (kg)} \times 60 \text{ min/}hr]}{\text{Final Concentration (1,000 ng/mL)}}$$

In some embodiments, the method of the invention reduces the risk of amputation by at least 10% when compared with standard of care treatments in frostbite. In some embodiments, the method of the invention reduces the risk of amputation by at least 15%, at least 20%, at least 25%, at least 30%, at least 35%, or at least 40% when compared with standard of care treatments in frostbite. In some embodiments, the method of the invention reduces the risk of amputation by at least 30% when compared with standard of care treatments in frostbite.

In some embodiments, standard of care for frostbite treatment includes rewarming as the first line of treatment. In some embodiments, rewarming is in conjunction with administration of aspirin and/or ibuprofen. In some embodiments, standard of care for frostbite treatment includes administration of thrombolytic therapy. In some embodiments, standard of care for frostbite treatment includes administration of tissue plasminogen activator (tPA). In some embodiments, standard of care for frostbite treatment includes administration of buflomedil.

In some embodiments, the method of the invention provides a safety profile in the subjects that is consistent with safety profile observed in systemic sclerosis subjects experiencing symptomatic digital ischemic episodes from multicenter, double-blind, randomized, placebo-controlled studies with iloprost continuous infusion. In some embodiments, the method of the invention provides a safety profile in the subjects that is consistent with safety profile observed in Example 2.

The present disclosure also relates to administering iloprost or a pharmaceutically acceptable salt thereof or a stereoisomer thereof to a frostbite patient comprising the steps of: i) transferring about 1 mL of about 100 mcg/mL concentrated solution of iloprost or pharmaceutically acceptable salt thereof into about 100 mL of 0.9% sodium chloride solution to provide an infusion solution of iloprost or pharmaceutically acceptable salt thereof; and ii) administering the infusion solution to the frostbite patient by infusion. In embodiments, the concentrated solution of iloprost or pharmaceutically acceptable salt thereof is in a single dose or single use vial in an amount of about 1 mL. In embodiments, the single dose or the single use vial is a glass vial.

EXAMPLES

The disclosure now being generally described, it will be more readily understood by reference to the following examples which are included merely for purposes of illustration of certain aspects and embodiments of the present invention, and are not intended to limit the invention.

Example 1. Efficacy of Iloprost for Treating of Frostbite

Frostbite is an injury caused by exposure of tissue to freezing temperatures. Severe frostbite may result in amputation leading to considerable morbidity. The objective was to identify and synthesize, via systematic literature review and meta-analysis (MA), evidence published on patient-level historical amputation rates in adults with severe frostbite treated with and without iloprost.

Methods: The literature review was conducted using Preferred Reporting Items for Systematic Reviews and Meta-Analyses (PRISMA) guidelines. It identified English-language articles published from Jan. 1, 2000 to Jul. 31, 2022 reporting amputation rates associated with iloprost and standard of care (SoC) treatments in severe frostbite. Study designs of interest were clinical trials (randomized and single arm), observational studies, and case series with at least 10 patients. MAs of proportions of patients with amputation were conducted. The published studies considered for the MA include:

A retrospective review of 199 patients with severe (grades 3-4) frostbite admitted to a level 1 trauma center in Colorado between 2015-2020 reported amputation rates of 49.8% in the overall population (n=199) and 59.8% in patients who did not receive thrombolytic therapy (n=127) (Carmichael et al., 2022).

A prospective observational study of 311 patients in a level 1 trauma center in Minnesota with frostbite injuries between 2014-2019 reported that, of 165 patients with severe frostbite, defined as post-rewarming perfusion deficit on imaging, 30.3% required amputation (Lacey et al., 2021). Thrombolytic therapy (tPA) was used in 75% of patients in this sample. In the subset not receiving tPA, the salvage rate was 53.4%.

A retrospective chart review study of 70 patients hospitalized for severe frostbite injuries was conducted at Chamonix Hospital in France from 1985 to 1999. In these patients, the calculated risk of amputation was reported to be 31%-67% for grade 3 frostbite (depending on the extent of the lesion to the intermediary or proximal phalanx), and 98%-100% for grade 4 frostbite (Cauchy et al., 2001).

In a retrospective review of 10 patients with deep frostbite sustained between November 2013 and March 2014 who were treated at a verified burn center in Chicago, IL, 9 (90%) patients required an amputation, which included partial or complete digital amputation or more proximal extremity amputation (Shenaq et al., 2019).

Nine patients with severe frostbite from 2000 to 2017 in the University of Michigan Health System (Ann Arbor, MI) who received non-thrombolytic management were identified by retrospective review (Patel et al., 2017). In this group, all patients (100%) had at least 1 digit amputated (average digits amputated per patient was 8.6, range: 4 min-14 max).

Seventy-three frostbite patients with severe injury from 2006 to 2014 were identified in the prospectively maintained database at a single urban burn and trauma center in Minneapolis, MN (Nygaard et al., 2017). Overall, 32 patients (44%) required amputation. In the group that received SoC treatment not including thrombolytic therapy, 16/28 (50%) of patients required amputations.

Twenty-six patients with severe frostbite injury from 1995 to 2006 were treated at a single burn center in Utah (Bruen et al., 2007). Bruen et al. reported 41% of digits impacted required amputation (97 out of 243 injured digits).

In historical controls (1985-1989) at a burn center in Minnesota, Twomey et al., 2005, reported half of patients (50%) treated with standard of care required amputation (8 of 16 patients).

Determination of Risk of Amputation: Table 1 discloses the historical amputation rates in severe frostbite patients. The studies listed in Table 1 was the basis of MA for determining the historical risk of amputation. A large variability in treatments included as SoC was noted. In the US, the SoC treatment for severe frostbite is likely to be best represented by the group of studies with "Severe", "Deep" or "grade 3-4" frostbite (or an explicit definition equivalent to these), excluding studies using alprostadil. Therefore, only such studies (n=8) were included in the meta-analysis as a "base-case" scenario.

The two studies that were the biggest outliers, both with proportions of patients with amputations below the mean, were Cauchy 2000 (23%) and Rogers 2022 (29%). Cauchy 2000 was likely impacted by the unknown proportion of patients who received iloprost and/or tPA and due to the use of a different frostbite severity rating system (compared with the other studies), as well as the unknown proportion of grade 3 vs 4 frostbite. For Rogers 2022, the low rate may be in part due to the extent of thrombolytic treatment, with nearly 80% of patients receiving tPA, with the time to thrombolytic treatment in the last year of patient accrual of 6.6 hours.

TABLE 1

Historical Amputation Rates in Patients with Severe Frostbite

| Reference | Type of Study, Country, and Dates of Study | Patient Population | Treatment After Rewarming | Amputation Rate |
|---|---|---|---|---|
| Carceller, 2019 | Retrospective observational; multinational; dates not reported | Mountaineers with frostbite (n = 91) | SoC, no tPA | 68 out of 91 patients (74.7%) |
| Carmichael, 2022 | Retrospective review; United States (Colorado); 2015-2020 | Severe (grades 3-4) frostbite (n = 199) | SoC, with or without tPA (n = 199) | 99 out of 199 patients (49.7%) |
| | | | SoC, no tPA (n = 127) | 76 out of 127 patients (59.8%) |

TABLE 1-continued

Historical Amputation Rates in Patients with Severe Frostbite

| Reference | Type of Study, Country, and Dates of Study | Patient Population | Treatment After Rewarming | Amputation Rate |
|---|---|---|---|---|
| Cauchy 2000 | Retrospective review; France; 1986-1999 | Severe frostbite (n = 92) | SoC | 21 out of 92 patients (22.8%) |
| Cauchy 2011 | Open label RCT; France; 1996-2008 | Severe (grades 3 or 4) frostbite (n = 46) Superficial (grade 2) frostbite (n = 1) | SoC with buflomedil (n = 15) | 9 out of 15 patients (60%) considered likely to receive amputation [a] |
| | | | SoC with iloprost (n = 16) | 0 patients considered likely to receive amputation [a] |
| | | | SoC with rtPA (n = 16) | 3 out of 15 patients (18.7%) considered likely to receive amputation [a] |
| Lindford, 2017 | Retrospective observational; Finland; 2013-2016 | Frostbite (n = 20), of which 14 had severe frostbite | SoC (superficial) (n = 6) | 0 patients with superficial frostbite underwent amputation |
| | | | SoC, no tPA or iloprost (severe) (n = 2) | Not specified |
| | | | SoC with tPA (n = 8) and with tPA and iloprost (n = 1) | 4 out of 9 patients (44.4%) The patient who received both tPA and iloprost had no amputation |
| | | | SoC with iloprost (n = 3) | Not specified |
| Nygaard, 2017 | Retrospective review; United States (Minnesota); 2006-2014 | Severe frostbite (n = 73) | SoC with or without tPA (n = 73) | 32 out of 73 patients (44%) |
| | | | SoC no tPA (n = 28) | 16 out of 28 patients (57%) |
| Rogers, 2022 | Retrospective review; United States | Severe frostbite (n = 208) | Thrombolytics (n = 142) | 61 out of 208 patients (29.3%) |
| Shenaq, 2019 | Retrospective review; United States (Illinois); 2013-2014 | Cold injuries (n = 53), of which n = 10 had "deep" frostbite | SoC, no tPA | 9 out of 10 patients with deep frostbite (90%) 26 out of 72 affected digits (36%) and 7 proximal amputations (trans metatarsal, Lisfranc, partial hand) |

Amputation rates for patients are based on the number of patients requiring amputation of at least 1 digit.
Amputation rates for digits are based on the number of digits requiring at least a partial amputation.
[a] Likelihood of amputation was determined by the presence of a radiotracer anomaly in at least one digit in the bone phase of technetium scintigraphy after 8 days of treatment
SoC = standard of care;
rtPA = recombinant tissue plasminogen activator;
tPA = tissue plasminogen activator Carceller, A. et al., (2019). Amputation Risk Factors in Severely Frostbitten Patients. International journal of environmental research and public health 16.
Carmichael, H. et al., (2022). Remote Delivery of Thrombolytics Prior to Transfer to a Regional Burn Center for Tissue Salvage in Frostbite. A Single-center Experience of 199 Patients. Journal of burn care & research: official publication of the American Burn Association 43, 54-60.
Cauchy, E. et al, (2000). The value of technetium 99 scintigraphy in the prognosis of amputation in severe frostbite injuries of the extremities. A retrospective study of 92 severe frostbite injuries. The Journal of hand surgery 25, 969-978.
Cauchy, E. et al., (2011). A controlled trial of a prostacyclin and rt-PA in the treatment of severe frostbite. N Engl J Med 364, 189-190.
Lindford, A. et al., (2017). The evolution of the Helsinki frostbite management protocol. Burns: Journal of the International Society for Burn Injuries 43, 1455-1463.
Nygaard, R. M. et al., (2017). Time Matters in Severe Frostbite. Assessment of Limb/Digit Salvage on the Individual Patient Level. Journal of burn care & research: official publication of the American Burn Association 38, 53-59.
Rogers, C. et al., (2022). The Effects of Rapid Rewarming on Tissue Salvage in Severe Frostbite Injury. Journal of burn care & research: official publication of the American Burn Association 43, 906-911.
Shenaq, D. S. et al., (2019). Urban Frostbite. Strategies for Limb Salvage. Journal of burn care & research: official publication of the American Burn Association 40, 613-619.

The literature review identified 17 primary studies; 16 were deemed eligible for the MAs of proportions. Results for pooled MA arm-level data for SoC estimated a 55% (95% confidence interval [CI]: 38%-71%; FIG. 1; RE=random effects) risk of a patient receiving at least one amputation. Tests for heterogeneity indicated high degree present with an $I^2$=93.8% and p-value<0.0001.

Efficacy-Proportion of Patients with Amputation: The systematic literature review (SLR) identified 2 studies reporting the proportion of patients with amputations after receiving iloprost (plus SoC) for frostbite (Cauchy et al., 2011; Cheguillaume, B. (2011). Controlled trial of iloprost and iloprost and rt-PA in the treatment of severe frostbite. Presented for the Award of DoctoralDegree in Medicine (Saint-Martin-d'Hères, France); Poole et al., (2021). Management of severe frostbite with iloprost, alteplase and heparin. A Yukon case series. CMAJ open 9, E585-E591). One of these studies reported amputation in zero patients out of 16 patients treated with iloprost (plus SoC), and amputation in 3 out of 16 patients who received iloprost plus rtPA (19%) (Cauchy et al., 2011; Cheguillaume, 2011), and 1 reported amputation in 4 out of 12 patients (33%) treated with iloprost (plus SoC, with or without alteplase and heparin) (Poole et al., 2021).

Sensitivity analyses reflect several ways of deriving the data (amputation rate for grade 3-4 frostbite) from the supplemental table in Cauchy 2011 (Cauchy et al., 2011). The first consideration was whether to include or exclude the patient receiving iloprost plus rtPA who was predicted to require amputation based on bone scan but was lost to follow-up. The second consideration was whether to combine the iloprost plus rtPA group with the iloprost alone group, or whether to only consider iloprost alone.

Figure 2:
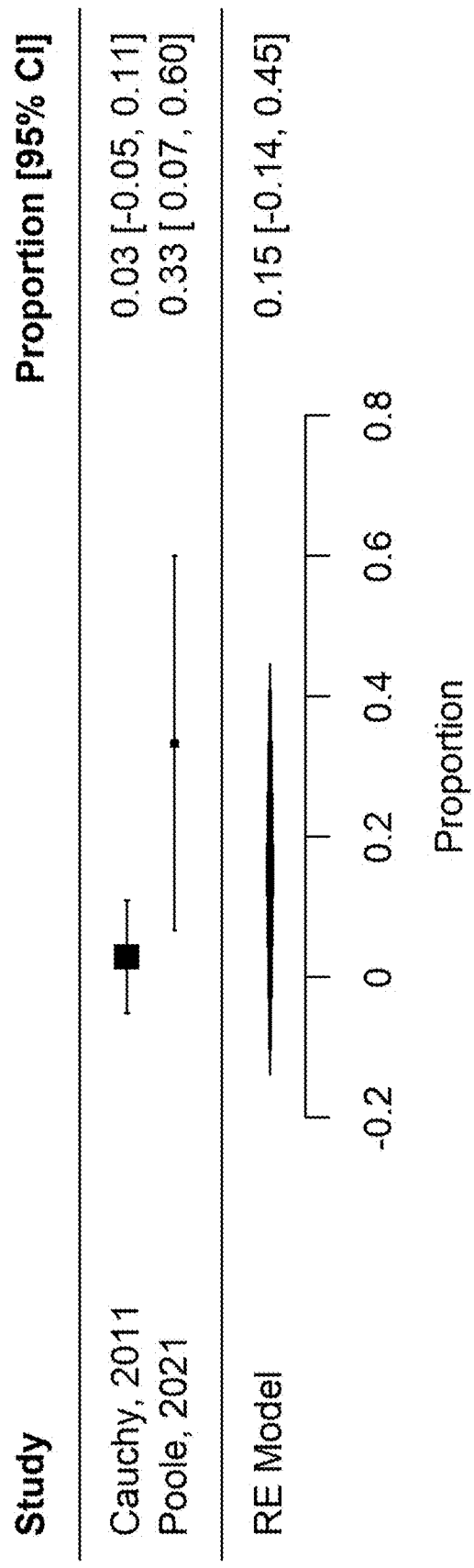
FIG. 2 shows proportion of patients with amputation after iloprost treatment for frostbite.

Results for pooled arm-level data for iloprost analyses found proportion of patients with amputation of 15% (95% CI: 0-45%) with high heterogeneity (I2=78.1%; Q p-value=0.0325; FIG. 2; RE=random effects). All of the other scenarios provided similar results for the estimated proportion of patients with amputation (15.4% to 18.0% for different scenarios), with large error bars for this estimate and high heterogeneity (I2 ranging from 63.1% to 78.1% for different scenarios).

Efficacy Proportion of Digits with Amputation: Data from 2 studies reporting the proportion of digits with amputations after receiving iloprost versus SoC for Grade 3/4 frostbite were included in the meta-analysis. Cauchy 2011 reported amputation in zero out of 78 digits treated with iloprost, and amputation in 40 out of 75 digits who received SoC (53.3%; Cauchy et al., 2011; Cheguillaume, 2011). When data for those receiving iloprost alone and iloprost+tPA were combined in Cauchy 2011 (n=177), the number of digit amputations went from zero to 3 (1.3%).

Crooks 2022 reported amputation in 62 out of 198 digits (31.1%) treated with iloprost versus 104 out of 185 digits treated with SoC (56.2%; Crooks et al., 2022). While the exact number of digits that received tPA is not specified, it was reported that only a minority of iloprost patients also received tPA (5 of 26) and a subgroup analysis showed that these patients had a higher chance of amputation compared to those receiving iloprost alone (p<0.05). As noted previously, there was an imbalance in the proportion of digits with Grade 3 vs Grade 4 frostbite between the 2 groups; of Grade 3-4 frostbite, Grade 4 frostbite was in only 23% of digits treated with SoC (43/185) versus 48% for iloprost (96/198). To address this imbalance, stratified odds-ratios and proportions were calculated for each study.

Figure 3:
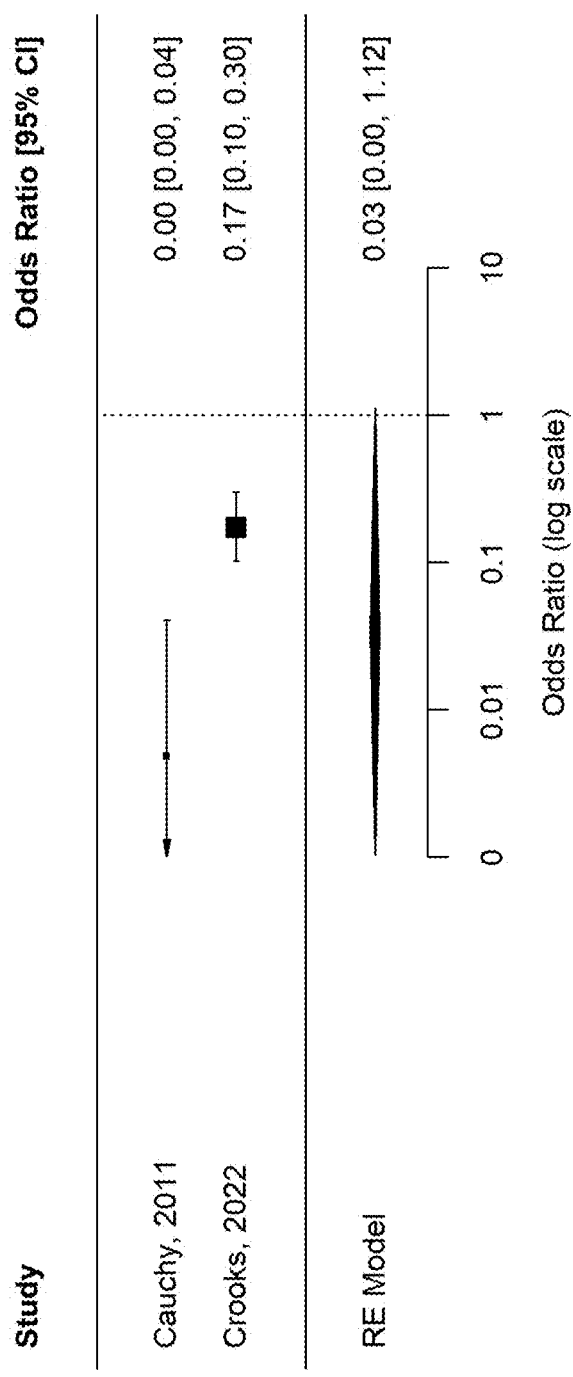
FIG. 3 shows digits amputated following treatment with iloprost alone vs standard of care.
Figure 4:
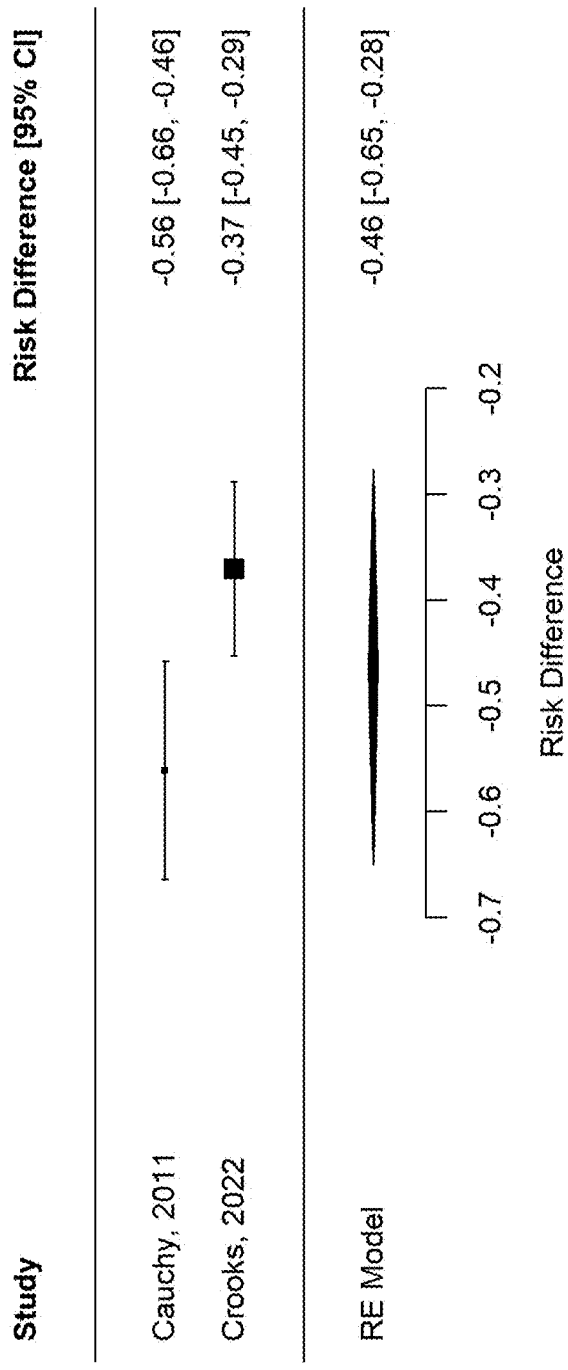
FIG. 4 shows digits amputated following treatment with iloprost alone and iloprost plus tPA vs standard of care.

When the 2 studies were meta-analyzed, the odds ratio (OR) for the base-case was 0.047 (95% CI: 0.002-0.966; p=0.047; FIG. 3; RE=random effects). When the iloprost+tPA patients in Cauchy 2011 (Cauchy et al., 2011; Cheguillaume, 2011) were added in, the result was similar (OR: 0.034, 95% CI: 0.001, 1.12; p=0.057; FIG. 4; RE=random effects). For both analyses, the heterogeneity was extremely high: I2=82.4% for the base-case and $I^2$=90.3% for the analysis including the patients with iloprost+tPA for both studies. This reflected that the odds ratios differed greatly between studies. While each study's individual odds ratio demonstrates a statistically significantly higher risk of digit amputation for SoC versus iloprost, the high between-study variance, and large within-study variances for Cauchy 2011 contribute to wide 95% CIs. These large variances, when combined, lead to the pooled analysis failing to show as strong a significant difference between treatments as found in the studies individually. Also, note that the employed model makes the common assumption that to the extent that underlying heterogeneity exists, it is symmetric and normally distributed. As these 95% intervals are based on such a normality assumption, they should be interpreted with caution in the presence of such heterogeneity.

The unadjusted (naïve) indirect comparisons in the meta-analysis consistently showed a 36% to 49% advantage for iloprost over SoC across a variety of scenarios, with the base-case result (targeting studies for which there was confidence that all patients had severe frostbite and did not receive alprostadil) with an advantage of 39% [95% CI: 6-73%, p=0.02]. That is, comparisons between iloprost and SoC showed a 39% reduction in amputation for iloprost.

Three iloprost studies reported safety data. Safety events associated with iloprost were generally mild and included headache, hot flushes/flushing, palpitations/tachycardia, and nausea and vomiting. These were managed symptomatically or by lowering iloprost dose, and rarely resulted in iloprost discontinuation.

Conclusion: Our literature review of the treatment of severe frostbite with either iloprost or SoC found a substantial rate of amputation with SoC and, comparatively, a significant reduction in amputation rate in patients treated with iloprost.

Example 2. A Multicenter, Double-Blind, Randomized, Placebo-Controlled, Study Evaluating Intravenous Iloprost in Subjects with Symptomatic Raynaud's Phenomenon Secondary to Systemic Sclerosis (SSc)—Evaluation of Safety of Iloprost This was a multicenter, double-blind, randomized, placebo-controlled study to provide an initial evaluation of the effect of iloprost on the symptomatic relief of RP attacks in subjects with SSc.

Subjects were randomized in a 1:1 ratio to iloprost injection for IV use or placebo. Randomization was stratified based on the use of phosphodiesterase inhibitors at screening. Study drug administration began on Day 1, and subjects received study drug for 5 consecutive days (e.g., Monday through Friday) as an IV infusion over 6 hours each day via a peripheral line (NovaCath™ Integrated IV Catheter System) or a peripherally inserted central catheter using an infusion pump.

Subjects must have had a systolic blood pressure ≥85 mmHg (sitting position) prior to study drug administration each day of administration. On Day 1, study drug was initiated at a starting dose of 0.5 ng/kg/min, and dose increases occurred every 30 minutes (±5 minutes) in increments of 0.5 ng/kg/min up to 2.0 ng/kg/min or the individual tolerated dose. If dose-limiting adverse events (e.g., headache, flushing, jaw pain, myalgia, nausea, or vomiting) occurred that could not be tolerated by the subject, or if the subject experienced symptomatic hypotension, then the dose was reduced in a step-wise manner by 0.5 ng/kg/min every 30 minutes (+5 minutes) until a tolerated dose was determined or the infusion was stopped until the symptoms resolved at which point the study drug was reinitiated at a previously tolerated dose. If symptomatic hypotension or a dose-limiting adverse event occurred during administration of iloprost at the starting dose (i.e., 0.5 ng/kg/min), the infusion was reduced to 0.25 ng/kg/min. If the dose of 0.25 ng/kg/min was not tolerated due to symptomatic hypotension or if a dose-limiting adverse event occurred, the study drug was discontinued, and re-initiation of the infusion could have been attempted after the event had resolved or had been treated. Blood pressure and heart rate were monitored 15 minutes (±5 minutes) prior to and after all dose changes. The maximum tolerated dose was maintained for the remaining 6-hour daily period. At the end of the 6-hour infusion period, the dose was stopped. Subjects were to be monitored for up to 1 hour after completion of study drug infusion (i.e., vital signs were obtained 15 minutes [±5 minutes] and 1 hour [±15 minutes] after completion of the infusion).

On Days 2 to 5, the infusion was started using the highest infusion rate tolerated on the previous day without up- or down-titration, unless the subject did not tolerate the infusion or adverse events occurred that could not be tolerated by the subject and necessitated a reduction in the dose. Vital signs were measured prior to study drug administration and at 15 minutes (±5 minutes) prior to and after all dose changes during the infusion. Additionally, vital signs were monitored at 15 minutes (±5 minutes) and 1 hour (±15 minutes) after completion of the 6-hour infusion.

During the treatment period (Days 1 to 5), while subjects received study drug, the electronic patient-reported outcomes (ePRO) diary was not completed. No study assessments were performed on the 2 days following the end of treatment (Days 6 and 7 [i.e., Saturday and Sunday]) to allow the subject to rest and return to a schedule of normal daily living activity following the 5 days of infusions.

Subjects were contacted via telephone on Day 8 to ensure they resumed completion of the daily ePRO diary; subjects completed the ePRO diary from Day 8 through Day 21. On Day 22, subjects returned to the clinic for post-treatment evaluations. A follow-up visit occurred 30 days after the last administration of study drug (Day 35).

Subjects who discontinued study drug early remained in the study (unless the subject withdrew consent) and completed the daily ePRO diary from Day 8 to Day 21, including clinical laboratory assessments on the remaining missed infusion days as well as post-treatment study assessments.

The total duration of the study for a subject was up to approximately 9 weeks.

Number of subjects: Randomized—34 subjects; Completed—34 subjects

Diagnosis and Main Criteria for Inclusion: The population for this study included male and female subjects ≥18 years of age who met the following criteria: had a diagnosis of SSc, as defined by the 2013 American College of Rheumatology criteria/European League Against Rheumatism criteria; had a diagnosis or history of RP, self-reported or reported by a physician, with at least a 2-phase color change in figure(s) of pallor, cyanosis, and/or reactive hyperemia in response to cold exposure or emotion; and had a minimum of 10 symptomatic RP attacks, documented in the ePRO diary, that occurred over at least 3 separate days of the 5-day eligibility period.

Investigational Product and Comparator Information: Iloprost injection for IV use and matching placebo were supplied in vials packaged in a blinded study drug kit (10 vials per kit). The iloprost and placebo vials were identical, except 100 mcg of iloprost was added to the active study drug vials. The drug product was diluted with sodium chloride 0.9% in a drug reservoir (IV bag) prior to use.

Safety parameters included adverse events, physical examination findings, vital sign measurements (heart rate and blood pressure), 12-lead electrocardiogram (ECG) findings, and standard clinical laboratory measurements (chemistry and hematology).

Summary of Safety Results:

No subjects experienced a serious adverse event (SAE), adverse event of special interest (AESI), treatment-emergent adverse event (TEAE) leading to discontinuation of study drug, or TEAE leading to death in this study.

Overall, 31 (91.2%) subjects experienced a TEAE: 14 (82.4%) subjects in the placebo group and 17 (100.0%) subjects in the iloprost group. The majority of TEAEs were considered mild to moderate in severity. Two (11.8%) subjects in the iloprost group experienced TEAEs that were considered severe by the Investigator.

The most commonly reported TEAEs (based on the total number of subjects who experienced this TEAE) were headache (21 [61.8%] subjects total: 5 [29.4%] subjects in the placebo group and 16 [94.1%] subjects in the iloprost group), nausea (14 [41.2%] subjects total: 3 [17.6%] subjects in the placebo group and 11 [64.7%] subjects in the iloprost group), abdominal pain (5 [14.7%] subjects total: 1 [5.9%] subject in the placebo group and 4 [23.5%] subjects in the iloprost group), and flushing (5 [14.7%] subjects total: 0 [0.0%] subjects in the placebo group and 5 [29.4%] subjects in the iloprost group).

There were no clinically significant changes in chemistry or hematology laboratory values during the study.

There were no TEAEs related to vital signs, physical examination findings, or ECGs in this study.

There were no hypertensive or hypotensive events reported in this study. There was no bradycardia or tachycardia reported in this study.

Conclusions:

The results confirmed that the iloprost dosing titration algorithm could be safely used in subjects. All adverse events related to the study drug as assessed by the Investigator were expected and consistent with the known safety profile of iloprost. There were no deaths, SAEs, AESIs, or TEAEs leading to study drug discontinuation during this study.

Example 3. Solution Stability of Fully Diluted Ready-to-Use Iloprost

Iloprost 100 μg/mL injection product is administered to patients by IV bag infusion over a period of six hours. The fully diluted ready to use iloprost is prepared in pharmacy cleanroom using sterile preparation standards (USP Chapter <797>) by pharmacy trained and licensed staff. The fully diluted ready to use drug product may be prepared several hours ahead of treatment with storage at ambient conditions or several days ahead of treatment with storage at refrigerated (2-8° C.) conditions. The IV bags are prepared using empty sterile IV bags which are filled with 99 mL of 0.9% NaCl and 1.0 mL of iloprost 100 μg/mL injection product.

The bags are then manually mixed gently to provide a uniform solution. Administration IV bags were prepared and stored at several conditions with routine sampling for assay testing for stability under i) 25° C./60% RH, ii) 5° C. for 5 days to 25° C./60% RH, iii) 5° C. for 8 days to 25° C./60% RH.

IV Bag Sample Preparation: Two 50 mL syringes with 18-gauge needles were assembled. 1.0 mL syringe with 18-gauge needle was assembled. Using a 50 ml syringe, 50 mL of 0.9% NaCl was transferred into an empty IV bag (sterile, ICU Medical) using the injection port. Using a second 50 ml syringe, 49 mL of 0.9% NaCl was transferred into the same IV bag using the injection port resulting in 99 mL of solution. Using the 1 ml syringe, 1.0 mL of iloprost 100 µg/mL injection product was transferred into the IV bag using the injection port. The needle was removed and the port was securely closed. The IV bag was gently inverted several times to mix. During inversion, it was occasionally paused to squeeze the injection port area to ensure liquid rinsed into area several times.

Sampling Procedure: For sampling, a 3 mL syringe was assembled with an 18-gauge needle. Using a 3 mL syringe, 2 mL of IV bag solution was withdrew through the injection port and 1 mL was transferred to a HPLC vial for neat injection and the other 1 mL was transferred to a back-up HPLC vial. HPLC vials were stored at refrigerated conditions 2-8° C.

Sample Storage and Sampling: For each testing conditions (i-iv discussed above), 12 IV bag samples were prepared (6 IV bags for condition ia)—see below for sampling time). For condition i), all 12 IV bags were then placed into 25° C./60% RH stability chamber ensuring each bag is resting on its largest surface area side. After the first time point, the IV bags were removed from the chamber and each IV bag was mixed by inversion several times. Sampling from each IV bag was taken for HPLC analysis. After sampling, the IV bags were placed back into 25° C./60% RH stability chamber ensuring each bag is resting on its largest surface area side, until next sampling time. At each sampling time, the IV bags were removed from the chamber and each IV bag was mixed by inversion several times before samples were removed.

For conditions ii) and iii), all 12 IV bags for each testing condition were placed into a 2-8° C. stability chamber ensuring each bag is resting on its largest surface area side. After 5 days have passed for condition ii) or after 8 days have passed for condition iii), the IV bags were removed from the chamber and allowed to equilibrate to room temperature. Each IV bag was mixed by inversion several times. Sampling from each IV bag was taken for HPLC analysis. Then the IV bags were placed in the 25° C./60% RH stability chamber and sampled at certain time points as discussed herein.

Sampling time for condition ia): 2 h, 4 h, 6 h, 8 h, and 24 h

Sampling time for ib): 8 h, 12 h, 48 h, and 96 h

Sampling time for condition ii): 5 days (at the end of storage in 2-8° C. stability chamber), 5 days and 8 h, and 5 days and 12 h Sampling time for condition iii): 8 days (at the end of storage in 2-8° C. stability chamber), 8 days and 8 h, and 8 days and 12 h Sample Analysis: Samples were analyzed by HPLC using a validated method (validation protocol not shown).

| | |
|---|---|
| HPLC Column: | Waters Spherisorb ODS-2, 125 mm, ×4.6 mm, 3 µm, P/N PSS832116 |
| Column Temperature: | 20° C. |
| Sample Temperature: | 5° C. |
| Flow Rate: | 1.0 mL/min |
| Injection Volume: | 100 µL |
| UV (DAD or MWD): | 200 nm, bandwidth 4 nm; Identification by UV Spectrum 200-400 nm |
| UV (VWD): | 200 nm |
| Run Time: | 55 Minutes |
| Needle Rinse: | (75:25 Milli-Q ™ Water:ACN) |
| Mobile Phase A: | (8 g/L BCD in 33% ACN, pH 2.0) |
| Mobile Phase B: | (50:50:0.1 Milli-Q ™ Water: ACN:H3PO4) |

| | Time (minutes) | % Mobile Phase A | % Mobile Phase B |
|---|---|---|---|
| Gradient: | 0 | 100 | 0 |
| | 30 | 100 | 0 |
| | 35 | 5 | 95 |
| | 50 | 5 | 95 |
| | 50.1 | 100 | 0 |
| | 55 | 100 | 0 |

The concentration of each sample per the equation below:

$$\text{Sample Concentration } (\mu g/mL) = \frac{Rsam}{Rstd} \times Cstd \text{ (mg/mL)} \times \frac{Vpip \text{ (mL)}}{Vstd \text{ (mL)}} \times 1000 \, \mu g/mg$$

Rstd=Average sum of the areas of the Iloprost peaks from five Standard Solution injections made during system suitability.

Rsam=Sum of the areas of the Iloprost peaks from the sample solution injection

Cstd (mg/mL)=Concentration of Iloprost Stock Standard Solution in mg/mL

Vstd (mL)=Volume of Standard Solution in mL (10 mL)

Vpip (mL)=Volume of Iloprost Stock Standard Solution pipetted into the Standard Solution in mL (0.1 mL)

The % Initial (initial concentration) of each stored sample was determined per the equation below:

$$\% \text{ Initial} = \frac{\text{Stored Sample Concentration } (\mu g/mL)}{\text{Initial } (T=0) \text{ SampleConcentration } (\mu g/mL)} \times 100$$

The results from the IV Bag stability study under condition ia (25° C./60% RH stability; sample time 2 h, 4 h, 6 h, 8 h, and 24 h) are presented in Table 1A. The % initial results for all of the IV bag preparations exhibited a range of 94.2-94.9%. These results were as expected from the nature of the IV bag preparation which was designed to mimic the clinical procedure. The IV bags were adjusted for volume to a target weight and then spiked with drug product using a disposable sterile 1 mL syringe equipped with a disposable sterile 18 gauge needle. A combination of variability in the weight of the IV bags and variability in the volume accuracy of the syringes and needles was expected to affect the accuracy of the spiking procedure. Each sample met the specification criterion of 90.0-110.0% and each stored sample was also within 90.0-110.0% of the initial result for the preparation.

TABLE 1A 24 hour stability at 25° C./60% RH

| Sample No. | Time-point (h) | Iloprost (%) | % Initial |
|---|---|---|---|
| 1 | Initial | 94.9 | |
|   | 2 | 95.3 | 100.4 |
|   | 4 | 96.7 | 101.9 |
|   | 6 | 95.4 | 100.6 |
|   | 8 | 94.8 | 99.9 |
|   | 24 | 97.0 | 102.2 |
| 2 | Initial | 94.2 | |
|   | 2 | 95.0 | 100.8 |
|   | 4 | 95.2 | 101.0 |
|   | 6 | 95.7 | 101.6 |
|   | 8 | 94.3 | 100.0 |
|   | 24 | 95.5 | 101.4 |
| 3 | Initial | 94.8 | |
|   | 2 | 94.2 | 99.4 |
|   | 4 | 94.3 | 99.5 |
|   | 6 | 95.0 | 100.2 |
|   | 8 | 94.8 | 100.0 |
|   | 24 | 96.7 | 102.0 |
| 4 | Initial | 94.6 | |
|   | 2 | 94.8 | 100.2 |
|   | 4 | 94.3 | 99.6 |
|   | 6 | 95.1 | 100.5 |
|   | 8 | 94.6 | 100.0 |
|   | 24 | 94.7 | 100.1 |
| 5 | Initial | 94.4 | |
|   | 2 | 94.2 | 99.7 |
|   | 4 | 94.7 | 100.3 |
|   | 6 | 93.7 | 99.3 |
|   | 8 | 96.2 | 101.9 |
|   | 24 | 93.4 | 98.9 |
| 6 | Initial | 94.3 | |
|   | 2 | 94.7 | 100.5 |
|   | 4 | 95.5 | 101.3 |
|   | 6 | 95.9 | 101.7 |
|   | 8 | 95.3 | 101.1 |
|   | 24 | 94.8 | 100.5 |

The results from the IV Bag stability study under condition ib (25° C./60% RH stability; sample time 8 h, 12 h, 48 h, and 96 h) are presented in Tables 1B and 1C. Each sample met the specification criterion of 90.0-110.0% and each stored sample was also within 90.0-110.0% of the initial result for the preparation.

TABLE 1B 96 hour stability at 25° C./60% RH (Batch 1)

| Time Point | Preparation | Iloprost (ng/mL) | % Initial |
|---|---|---|---|
| Initial (T = 0) | 1 | 977.49068 | — |
|   | 2 | 968.66746 | |
|   | 3 | 942.80790 | |
|   | 4 | 994.14641 | |
|   | 5 | 981.91733 | |
|   | 6 | 975.78016 | |

TABLE 1B-continued 96 hour stability at 25° C./60% RH (Batch 1)

| Time Point | Preparation | Iloprost (ng/mL) | % Initial |
|---|---|---|---|
| 8 hr | 1 | 973.57406 | 100 |
|   | 2 | 1009.87852 | 104 |
|   | 3 | 979.46989 | 104 |
|   | 4 | 1002.63999 | 101 |
|   | 5 | 977.22453 | 100 |
|   | 6 | 1007.06584 | 103 |
| 12 hr | 1 | 1004.19286 | 103 |
|   | 2 | 1008.58278 | 104 |
|   | 3 | 978.15686 | 104 |
|   | 4 | 1042.47061 | 105 |
|   | 5 | 975.06820 | 99 |
|   | 6 | 1005.44196 | 103 |
| 48 hr | 1 | 1003.58363 | 103 |
|   | 2 | 995.23565 | 103 |
|   | 3 | 968.03688 | 103 |
|   | 4 | 1001.02390 | 101 |
|   | 5 | 984.61614 | 100 |
|   | 6 | 977.30241 | 100 |
| 96 hr | 1 | 1013.28284 | 104 |
|   | 2 | 1017.49428 | 105 |
|   | 3 | 970.92026 | 103 |
|   | 4 | 1014.14964 | 102 |
|   | 5 | 994.07339 | 101 |
|   | 6 | 971.53175 | 100 |

TABLE 1C 96 hour stability at 25° C./60% RH (Batch 2)

| Time Point | Preparation | Iloprost (ng/mL) | % Initial |
|---|---|---|---|
| Initial (T = 0) | 1 | 980.86863 | — |
|   | 2 | 990.69772 | |
|   | 3 | 980.65678 | |
|   | 4 | 994.36439 | |
|   | 5 | 1000.53816 | |
|   | 6 | 1020.67367 | |
| 8 hr | 1 | 995.76595 | 102 |
|   | 2 | 1002.10267 | 101 |
|   | 3 | 994.55360 | 101 |
|   | 4 | 1003.76351 | 101 |
|   | 5 | 998.77363 | 100 |
|   | 6 | 983.28166 | 96 |
| 12 hr | 1 | 993.30159 | 101 |
|   | 2 | 984.11952 | 99 |
|   | 3 | 984.12486 | 100 |
|   | 4 | 989.62285 | 100 |
|   | 5 | 994.77764 | 99 |
|   | 6 | 1004.99733 | 98 |
| 48 hr | 1 | 993.66797 | 101 |
|   | 2 | 984.23731 | 99 |
|   | 3 | 994.36502 | 101 |
|   | 4 | 1031.78023 | 104 |
|   | 5 | 1005.03600 | 100 |
|   | 6 | 1014.71909 | 99 |
| 96 hr | 1 | 1002.16769 | 102 |
|   | 2 | 979.52872 | 99 |
|   | 3 | 988.97656 | 101 |
|   | 4 | 1004.97292 | 101 |
|   | 5 | 996.34817 | 100 |
|   | 6 | 1027.43687 | 101 |

The results from the IV Bag stability study under condition ii (5° C. for 5 days to 25° C./60% RH) are presented in Tables 1D and 1E. Each sample met the specification criterion of 90.0-110.0% and each stored sample was also within 90.0-110.0% of the initial result for the preparation.

TABLE 1D

5° C. for 5 days to 25° C./60% RH (Batch 1)

| Time Point | Preparation | Iloprost (ng/ml) | % Initial |
|---|---|---|---|
| Initial | 1 | 1007.32936 | — |
| (T = 0) | 2 | 953.59154 | |
| | 3 | 1014.73720 | |
| | 4 | 1019.54404 | |
| | 5 | 1036.25326 | |
| | 6 | 996.56811 | |
| 5° C. for 5 | 1 | 1049.58766 | 104 |
| days | 2 | 931.91928 | 98 |
| | 3 | 1023.92132 | 101 |
| | 4 | 1020.05717 | 100 |
| | 5 | 1024.17465 | 99 |
| | 6 | 1000.90608 | 100 |
| 5° C. for 5 | 1 | 1002.17085 | 99 |
| days | 2 | 957.27263 | 100 |
| 25° C./60% | 3 | 993.78991 | 98 |
| RH for 8 hr | 4 | 1040.15942 | 102 |
| | 5 | 1025.38946 | 99 |
| | 6 | 1010.55688 | 101 |
| 5° C. for 5 | 1 | 976.52119 | 97 |
| days | 2 | 943.23563 | 99 |
| 25° C./60% | 3 | 1015.06188 | 100 |
| RH for 12 hr | 4 | 1030.59268 | 101 |
| | 5 | 1010.05028 | 97 |
| | 6 | 982.68256 | 99 |

TABLE 1E

5° C. for 5 days to 25° C./60% RH (Batch 2)

| Time Point | Preparation | Iloprost (ng/mL) | % Initial |
|---|---|---|---|
| Initial | 1 | 1011.00891 | — |
| (T = 0) | 2 | 986.02971 | |
| | 3 | 1021.90645 | |
| | 4 | 1021.61212 | |
| | 5 | 1001.14785 | |
| | 6 | 988.43978 | |
| 5° C. for 5 | 1 | 1026.46301 | 102 |
| days | 2 | 1008.56452 | 102 |
| | 3 | 1024.57969 | 100 |
| | 4 | 1029.90237 | 101 |
| | 5 | 1011.12281 | 101 |
| | 6 | 987.37008 | 100 |
| 5° C. for 5 | 1 | 1023.49747 | 101 |
| days | 2 | 973.07617 | 99 |
| 25° C./60% | 3 | 1013.01926 | 99 |
| RH for 8 hr | 4 | 1011.71269 | 99 |
| | 5 | 996.65926 | 100 |
| | 6 | 970.82806 | 98 |
| 5° C. for 5 | 1 | 1022.38730 | 101 |
| days | 2 | 963.28102 | 98 |
| 25° C./60% | 3 | 1001.36417 | 98 |
| RH for 12 hr | 4 | 1003.23343 | 98 |
| | 5 | 1016.70001 | 102 |
| | 6 | 985.93577 | 100 |

The results from the IV Bag stability study under condition iii (5° C. for 8 days to 25° C./60% RH) are presented in Tables 1F and 1G. Each sample met the specification criterion of 90.0-110.0% and each stored sample was also within 90.0-110.0% of the initial result for the preparation.

TABLE 1F

5° C. for 8 days to 25° C./60% RH (Batch 1)

| Time Point | Preparation | Iloprost (ng/mL) | % Initial |
|---|---|---|---|
| Initial | 1 | 970.11915 | — |
| (T = 0) | 2 | 966.13069 | |
| | 3 | 989.59242 | |

TABLE 1F-continued

5° C. for 8 days to 25° C./60% RH (Batch 1)

| Time Point | Preparation | Iloprost (ng/mL) | % Initial |
|---|---|---|---|
| | 4 | 959.55241 | |
| | 5 | 964.81219 | |
| | 6 | 957.61598 | |
| 5° C. for 5 | 1 | 994.43539 | 103 |
| days | 2 | 953.18657 | 99 |
| | 3 | 978.41500 | 99 |
| | 4 | 953.14379 | 99 |
| | 5 | 984.18557 | 102 |
| | 6 | 956.73023 | 100 |
| 5° C. for 8 | 1 | 963.52003 | 99 |
| days | 2 | 955.94360 | 99 |
| 25° C./60% | 3 | 967.83409 | 98 |
| RH for 8 hr | 4 | 938.70012 | 98 |
| | 5 | 1032.99481 | 107 |
| | 6 | 961.84780 | 100 |
| 5° C. for 8 | 1 | 980.47291 | 101 |
| days | 2 | 964.06225 | 100 |
| 25° C./60% | 3 | 986.44359 | 100 |
| RH for 12 hr | 4 | 967.53103 | 101 |
| | 5 | 964.22470 | 100 |
| | 6 | 952.01922 | 99 |

TABLE 1G

5° C. for 8 days to 25° C./60% RH (Batch 2)

| Time Point | Preparation | Iloprost (ng/mL) | % Initial |
|---|---|---|---|
| Initial | 1 | 979.57170 | — |
| (T = 0) | 2 | 983.59476 | |
| | 3 | 998.93472 | |
| | 4 | 1008.63220 | |
| | 5 | 1025.59384 | |
| | 6 | 992.74821 | |
| 5° C. for 5 | 1 | 970.13301 | 99 |
| days | 2 | 957.91301 | 97 |
| | 3 | 1019.54124 | 102 |
| | 4 | 1006.94224 | 100 |
| | 5 | 993.60327 | 97 |
| | 6 | 1014.48560 | 102 |
| 5° C. for 8 | 1 | 983.93098 | 100 |
| days | 2 | 964.53372 | 98 |
| 25° C./60% | 3 | 1004.08143 | 101 |
| RH for 8 hr | 4 | 997.60330 | 99 |
| | 5 | 1010.96396 | 99 |
| | 6 | 1010.24659 | 102 |
| 5° C. for 8 | 1 | 967.45808 | 99 |
| days | 2 | 964.40986 | 98 |
| 25° C./60% | 3 | 1006.95543 | 101 |
| RH for 12 hr | 4 | 1011.04730 | 100 |
| | 5 | 1012.62453 | 99 |
| | 6 | 1008.92483 | 102 |

During the study, three unknown peaks in chromatograms were observed; however, all of these unknown peaks were present in control or stressed blank IV bag samples indicating that all unknown peaks were IV bag or saline related and were not caused by Iloprost drug product. The unknown peaks did not interfere with quantitation of Iloprost peaks and therefore the administration stability study is not considered to be impacted by the presence of the peaks.

These results indicate that the iloprost drug product exhibits suitable stability in the IV bags to support IV bag treatment and administration design.

Example 4. Study of Microbial Attribute of Iloprost 100 µg/mL Injection Composition The aim of this in-use stability study is to provide data reflecting the microbiological quality of iloprost 100 µg/mL injection composition and iloprost placebo injection composition after their preparation and storage under controlled storage conditions for a specific period of time. These composition preparation and storage simulates their preparation and storage conditions in compounding pharmacy prior to patient administration.

Iloprost 100 µg/mL injection composition and iloprost placebo injection composition samples are prepared (diluted in saline IV bags), stored under controlled conditions and tested at specific time points (day 0, day 10, and day 16). The prepared samples are assessed side-by-side with prepared samples that have been inoculated with a low level of bioburden (10-100 CFU/mL). The low level of bioburden is intended to simulate a microbial contamination at the time of container closure penetration. This microbial challenge study helps determine if the diluted ready to use products have any growth-promoting properties. Growth-promoting properties of these two drug products are assessed according to the USP <51> guidance.

Microbial counts of the inoculated products at time zero is compared to their microbial counts at day 10 and day 16. If the microbial counts on day 10 and day 16 are not higher than 0.5 log 10 unit compared to the starting microbial counts then, the drug products are considered non-growth-promoting and the storage conditions (time and temperature) are deemed appropriate for ensuring that the diluted ready to use drug products are safe.

This in-use stability study is designed and executed per the following guidelines:

The current United States Pharmacopeia General Chapters USP <51>, "Antimicrobial Effectiveness testing"

The CDER guidance on the subject by Metcalfe John W. (2009)

The CDER Microbiology Issues: A deep Dive by Candace Gomez-Broughton, "Aseptic Processing of Biological Products: Current Regulatory Issues", August 2018

The World Health Organization guidance on the subject: WHO Technical Report Series, No. 863, 1996, Annex 5

The Procedures Outlined in this Protocol

Scope: This protocol applies to microbiological testing in support of the microbiological stability of the diluted ready to use iloprost 100 µg/mL injection composition and iloprost placebo injection composition. The stability of these two drug products is assessed after penetration of the container and closure system for dose preparation and storage under controlled conditions. The preparation and storage conditions of the two drug products simulate the preparation and storage prior to patient administration. This protocol describes the study design and Bioburden testing using representative samples of iloprost 100 µg/mL injection composition and iloprost placebo injection composition samples.

Interpretation of Results: Initial microbial count (CFU/mL) for each inoculated sample is defined as the microbial count of that sample at time zero and determined by filtration test method. Growth or its absence thereof for a sample/microorganism combination at a specific time point is assessed in relation to time zero. Microbial count is determined for each microorganism at time zero and the log 10 of that microbial count will be calculated. Microbial count for each test sample will be determined at the specific time point, log 10 of that microbial count is calculated and compared to its microbial count log 10 value at time zero. If the difference between the two log 10 values is not more than half log 10 unit, the sample is not displaying microbial growth increase.

Iloprost 100 µg/mL injection composition preparation: Two 50 mL syringes with 18-gauge needles are assembled. 1.0 mL syringe with 18-gauge needle is assembled. Using a 50 mL syringe, 49 mL of 0.9% NaCl is transferred into an empty IV bag using the injection port. Using a second 50 ml syringe, 50 mL of 0.9% NaCl is transferred into the same IV bag using the injection port. Using the 1 ml syringe, 1.0 mL of iloprost 100 µg/mL injection product is transferred into the IV bag using the injection port. The needle was removed and the port was securely closed. The IV bag is gently inverted several times to mix. During inversion, occasionally paused to squeeze the injection port area to ensure liquid rinsed into area several times. Prepare total of 7 IV bags by this method.

Microbial Inoculation:

*S. aureus, B. subtilis, P. aeruginosa, C. albicans, A. brasiliensis*, and *E. coli* are used. Patheon frozen cultures, freshly harvested suspensions, or enumerated lyophilized microorganism preparations are used. Microorganisms that are not more than five passages removed from the master seed lot are used.

Test Samples: Using the appropriate syringe size and an 18-gauge needle, inoculate (inject through injection port) each IV bag and each IV bag of positive control with the appropriate microorganism suspension so that the inoculated IV bag contains between 5-10 CFU/mL (for a total of 500 to 1000 CFU/IV bag). Gently invert each IV bag several times to mix. During inversion, pause occasionally to squeeze the injection port area to ensure liquid rinses into area several times.

Inoculum Verification (perform in duplicate for each microorganism at time zero): Add 1 mL from each positive control sample to each of two 100×15 mm Petri dishes. Pour approximately 25 mL Letheen agar cooled to ≤45° C. into each of two Petri dishes and swirl to mix. Allow the agar to solidify and invert the plates to incubate. Incubate the bacteria plates at 30 to 35° C. for 3-5 days. Incubate Candia *albicans* plates at 20-25° C. for 3 to 5 days and incubate the *Aspergillus brasiliensis* plates at 20-25° C. for 3 to 7 days.

Sampling: Day 0 samples are taken immediately after the IV bags were prepared. Test samples are taken after 10 days and 16 days storage of the inoculated bags at 2-8° C. At the specified time point, assemble a 50 ml syringe with 18-gauge needle. Using the 50 mL syringe, withdraw 25 mL from each of the inoculated IV bags through the injection port and transfer to an appropriate size sterile test tube with cap. After taking the test samples, place the inoculated IV bags at 2-8° C. until the next sampling time point.

Testing Samples: Test the inoculated product samples, positive controls, product negative controls (iloprost and diluent), and diluent negative control. Each sample is tested in duplicate (two filters will be used). Prewash each of two sterile filter membranes with 100 mL Dilution Fluid D. Add a 10 mL aliquot of the test sample (inoculated drug product, product negative control, positive control or diluent negative control) to each filter unit and filter through. Wash each filter with 3×100 mL aliquots of Dilution Fluid D. Aseptically transfer the two filters to two separate Letheen Agar plates. Allow the agar to solidify and incubate as follows:

a. The inoculated product samples, and the positive control samples containing bacteria at 30 to 35° C. for 3 to 5 days.

b. The inoculated product samples, and the positive control samples containing Candia *albicans* at 20-25° C. for 3 to 5 days c. The inoculated product samples, and the positive control samples containing *Aspergillus brasiliensis* at 20-25° C. for 3 to 7 days.

d. The product and diluent negative controls: From each set, incubate one plate at 30-35° C. and one plate at 20-25° C. for as long as the test samples but not more than 7 days.

Rinse Fluid Negative Controls: Add 100 mL Dilution Fluid D to each of 2 sterile filter units and filter through. Aseptically transfer the two filters to two plates of Letheen agar. Incubate one plate at 30-35° C. and the other plate at 20-25° C. for as long as the test samples but not more than 7 days.

Agar Negative Controls: Incubate one plate of Letheen agar at 30-35° C. and the other plate at 20-25° C. for as long as the test samples but not more than 7 days.

Analysis: Count the Colony Forming Units (CFU) on each plate per SOP-QC-280 and calculate the arithmetic mean for each set of two plates. Calculate the percent recovery by dividing the mean of the product plate counts (CFU) by the mean of the positive control plate counts (CFU). Multiply by 100 and round to the nearest whole number.

$$\% \text{ Recovery} = \frac{\text{Mean of inoculated Product plates count } (CFU) \times 100}{\text{Mean of inoculated positive controls plates count } (CFU)}$$

Acceptance Criteria:

The percent recovery of the product test plates, at time zero, should be at least 50% of the positive controls mean. If lower recoveries (less than 50%) are observed, modify the method in order to overcome inhibition by utilizing one or more of the following:

Incorporate Neutralizing/Dispersing Agents into the Plating Medium or Rinse Fluid Utilize Different Media Each inoculum verification plate must have ≥1 CFU and ≤100 CFU There must be no growth on the agar and rinse fluid negative controls. A media or rinse fluid negative control failure requires an investigation to evaluate the impact to the testing described herein.

Results:

Microbial Enumeration Test Method Suitability. Suitability of the microbial enumeration test method was assessed at time zero by comparing the microbial recoveries from the diluted-ready-to use products to the microbial recoveries from the diluent (positive control). The method was considered suitable if the following criteria were met:
1. Each inoculum verification plate must have ≥1 CFU and ≤100 CFU
2. There must be no growth on the product negative controls, agar negative controls and rinse fluid negative controls.
3. The microbial recovery from the diluted-ready-to use products is at least 50% of the recovery from the diluent (positive control)

Each of the inoculum verification plate (*S. aureus, B. subtilis, P. aeruginosa, C. albicans, A. brasiliensis,* and *E. coli*) counts met the acceptance criteria: ≥1 and ≤100 CFU. All media, diluent and dilution fluid D negative controls exhibited no growth. All product negative controls exhibited no growth.

The recoveries of *S. aureus, B. subtilis, P. aeruginosa, C. albicans, A. brasiliensis,* and *E. coli* from iloprost 100 µg/mL injection composition and iloprost placebo injection composition samples, respectively, were all above 50% of the positive control recovery.

Assessment of growth-promoting properties of iloprost 100 µg/mL injection composition and iloprost placebo injection composition samples. Microbial counts were determined for each sample/microorganism combination at each time point, and the log 10 of the microbial count mean was calculated. The difference between the log 10 value (time X and time zero) was used to assess if the product is growth-promoting or not. The products were deemed non-growth promoting as assessed by this testing if the following criteria were met:
1. In accordance with USP <51>, for each tested microorganism there must be no microbial count increase that is higher than 0.5 log 10 relative to microbial counts at time zero.
2. There must be no growth on the product negative controls, agar negative controls and rinse fluid negative controls.

Results for each microorganism are summarized in the Tables 2A-2F.

$\text{Log}_{10}$ difference=$\log_{10}$ value at time X–$\log_{10}$ value at time 0

For each of *S. aureus, B. subtilis, P. aeruginosa, C. albicans, A. brasiliensis,* and *E. coli*, the $\log_{10}$ difference for each time point was not greater than 0.5 log 10 unit from time zero. Ready-to use iloprost 100 µg/mL injection composition and iloprost placebo injection composition do not promote *S. aureus, B. subtilis, P. aeruginosa, C. albicans, A. brasiliensis,* and *E. coli* growth when stored at 2-8° C. for up to 16 days.

The results presented in Tables 2A-2F show that the tested ready-to use iloprost 100 µg/mL injection composition and iloprost placebo injection composition do not display any growth-promoting properties towards the tested microorganisms: *S. aureus, B. subtilis, P. aeruginosa, C. albicans, A. brasiliensis,* and *E. coli*. This test meets the acceptance criteria for the assessment of growth-promoting properties of both iloprost 100 µg/mL injection composition and iloprost placebo injection composition.

TABLE 2A $\text{Log}_{10}$ comparison for *A. brasiliensis*

| Batch | Time point | Mean Microbial Count (CFU) | $\text{Log}_{10}$ of Microbial Count | Log difference compared to Time 0 |
|---|---|---|---|---|
| 1 | Day 0 | 50 | 1.6990 | |
| | Day 10 | 45 | 1.6532 | −0.0458 |
| | Day 16 | 47 | 1.6721 | −0.0269 |
| 2 | Day 0 | 47 | 1.6721 | |
| | Day 10 | 50 | 1.6990 | 0.0269 |
| | Day 16 | 47 | 1.6721 | 0 |
| 3 | Day 0 | 44 | 1.6435 | |
| | Day 10 | 57 | 1.7559 | 0.1124 |
| | Day 16 | 48 | 1.6812 | 0.0377 |
| 4 | Day 0 | 48 | 1.6812 | |
| | Day 10 | 45 | 1.6532 | −0.0280 |
| | Day 16 | 59 | 1.7709 | 0.0897 |

TABLE 2B $\text{Log}_{10}$ comparison for *C. albicans*

| Batch | Time point | Mean Microbial Count (CFU) | $\text{Log}_{10}$ of Microbial Count | Log difference compared to Time 0 |
|---|---|---|---|---|
| 1 | Day 0 | 30 | 1.4771 | |
| | Day 10 | 5 | 0.6990 | −0.7781 |
| | Day 16 | 1 | 0 | −1.4771 |

TABLE 2B-continued

Log$_{10}$ comparison for *C. albicans*

| Batch | Time point | Mean Microbial Count (CFU) | Log$_{10}$ of Microbial Count | Log difference compared to Time 0 |
|---|---|---|---|---|
| 2 | Day 0 | 48 | 1.6812 | |
| | Day 10 | 2 | 0.3010 | −1.3802 |
| | Day 16 | 1 | 0 | −1.6812 |
| 3 | Day 0 | 44 | 1.6435 | |
| | Day 10 | 2 | 0.3010 | −1.3425 |
| | Day 16 | 0 | No growth | N/A |
| 4 | Day 0 | 38 | 1.5798 | |
| | Day 10 | 1 | 0 | −1.5798 |
| | Day 16 | 1 | 0 | −1.5798 |

TABLE 2C

Log$_{10}$ comparison for *E. coli*

| Batch | Time point | Mean Microbial Count (CFU) | Log$_{10}$ of Microbial Count | Log difference compared to Time 0 |
|---|---|---|---|---|
| 1 | Day 0 | 61 | 1.7853 | |
| | Day 10 | 26 | 1.4150 | −0.3703 |
| | Day 16 | 16 | 1.2041 | −0.5812 |
| 2 | Day 0 | 58 | 1.7634 | |
| | Day 10 | 30 | 1.4771 | −0.2863 |
| | Day 16 | 12 | 1.0792 | −0.6842 |
| 3 | Day 0 | 32 | 1.5051 | |
| | Day 10 | 12 | 1.0792 | −0.4259 |
| | Day 16 | 9 | 0.9542 | −0.5509 |
| 4 | Day 0 | 73 | 1.8633 | |
| | Day 10 | 22 | 1.3424 | −0.5209 |
| | Day 16 | 11 | 1.0414 | −0.8219 |

TABLE 2D

Log$_{10}$ comparison for *P. aeruginosa*

| Batch | Time point | Mean Microbial Count (CFU) | Log$_{10}$ of Microbial Count | Log difference compared to Time 0 |
|---|---|---|---|---|
| 1 | Day 0 | 31 | 1.4914 | |
| | Day 10 | 0 | No growth | N/A |
| | Day 16 | 0 | No growth | N/A |
| 2 | Day 0 | 26 | 1.4150 | |
| | Day 10 | 1 | 0 | −1.4150 |
| | Day 16 | 0 | No growth | N/A |
| 3 | Day 0 | 25 | 1.3979 | |
| | Day 10 | 1 | 0 | −1.3979 |
| | Day 16 | 0 | No growth | N/A |
| 4 | Day 0 | 33 | 1.5185 | |
| | Day 10 | 0 | No growth | N/A |
| | Day 16 | 0 | No growth | N/A |

TABLE 2E

Log$_{10}$ comparison for *S. aureus*

| Batch | Time point | Mean Microbial Count (CFU) | Log$_{10}$ of Microbial Count | Log difference compared to Time 0 |
|---|---|---|---|---|
| 1 | Day 0 | 48 | 1.6812 | |
| | Day 10 | 16 | 1.2041 | −0.4771 |
| | Day 16 | 8 | 0.9031 | −0.7781 |
| 2 | Day 0 | 39 | 1.5911 | |
| | Day 10 | 18 | 1.2553 | −0.3358 |
| | Day 16 | 3 | 0.4771 | −1.114 |
| 3 | Day 0 | 52 | 1.7160 | |
| | Day 10 | 15 | 1.1761 | −0.5399 |
| | Day 16 | 6 | 0.7782 | −0.9378 |
| 4 | Day 0 | 51 | 1.7076 | |
| | Day 10 | 20 | 1.3010 | −0.4066 |
| | Day 16 | 2 | 0.3010 | −1.4066 |

TABLE 2F

Log$_{10}$ comparison for *B. subtilis*

| Batch | Time point | Mean Microbial Count (CFU) | Log$_{10}$ of Microbial Count | Log difference compared to Time 0 |
|---|---|---|---|---|
| 1 | Day 0 | 67 | 1.8261 | |
| | Day 10 | 32 | 1.5051 | −0.3210 |
| | Day 16 | 15 | 1.1761 | −0.6500 |
| 2 | Day 0 | 68 | 1.8325 | |
| | Day 10 | 30 | 1.4771 | −0.3554 |
| | Day 16 | 14 | 1.1461 | −0.6864 |
| 3 | Day 0 | 53 | 1.7243 | |
| | Day 10 | 23 | 1.3617 | −0.3626 |
| | Day 16 | 15 | 1.1761 | −0.5482 |
| 4 | Day 0 | 55 | 1.7404 | |
| | Day 10 | 26 | 1.4150 | −0.3254 |
| | Day 16 | 11 | 1.0414 | −0.6990 |

The disclosures of all publications, patents, patent applications and published patent applications referred to herein by an identifying citation are hereby incorporated herein by reference in their entirety.

In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A method of treating severe frostbite in a subject, comprising
   a) diluting about 1 mL of a pre-dilution composition comprising a concentrated solution of iloprost, said concentrated solution of iloprost comprising (1) about 0.1 mg/mL of iloprost, or a pharmaceutically acceptable salt or a stereoisomer thereof, (ii) about 0.24 mg/mL of tromethamine, (iii) sodium chloride, and (iv) ethanol, in 0.9% sodium chloride, said diluted composition having a final concentration of about 1 μg/mL of iloprost, or a pharmaceutically acceptable salt or a stereoisomer thereof; and
   b) administering the diluted composition to the subject by intravenous infusion, wherein the administration comprises a titration step on a first day of administration, said titration step being repeated on the second and third days of administration;
   wherein the administration on the first day comprises a starting dose and increments by which the dose is increased to a maximum dose, and wherein the administration on the second and third days comprises the same starting dose and increments of increase as on the first day, but wherein the maximum dose achieved on each day may be different;

wherein the diluted composition is administered to the subject for a maximum of 8 consecutive days; and wherein the method reduces the risk of digit amputation in the subject when compared with standard of care treatments for severe frostbite.

2. The method of claim 1, wherein the administering is at one or more doses between about 0.25 ng/kg/min and about 2.0 ng/kg/min.

3. The method of claim 1, wherein the administering comprises a titration step on a first day of administration with a starting dose of about 0.25 ng/kg/min or about 0.5 ng/kg/min.

4. The method of claim 3, wherein the starting dose is about 0.5 ng/kg/min, and wherein the subject does not have a pre-existing Child-Pugh Class B or Child-Pugh Class C hepatic impairment.

5. The method of claim 3, wherein the starting dose is about 0.5 ng/kg/min and the dose is decreased to about 0.25 ng/kg/min at the beginning of the titration step when the subject has a renal impairment with eGFR less than 30 mL/min/m$^2$ and the subject cannot tolerate the starting dose of about 0.5 ng/kg/min.

6. The method of claim 3, wherein the starting dose is about 0.25 ng/kg/min, and wherein the subject has a Child-Pugh Class B or Child-Pugh Class C hepatic impairment.

7. The method of claim 3, wherein the dose is increased in increments of about 0.5 ng/kg/min every about 30 minutes during the titration step until a maximum dose is reached.

8. The method of claim 7, wherein the maximum dose is about 2.0 ng/kg/min or a highest dose the subject can tolerate between about 0.25 ng/kg/min and about 2.0 ng/kg/min.

9. The method of claim 3, wherein the titration step comprises decrease in the dose if the subject has a dose-limiting reaction.

10. The method of claim 1, wherein the diluted composition is administered continuously each day during a treatment period, wherein the continuous administration per day is for about 6 hours.

11. The method of claim 8, wherein the maximum dose or highest dose is maintained for the remainder of a treatment period after performing the titration step on the first day, the second day, and the third day.

12. The method of claim 1, wherein the severe frostbite is a stage 3 or a stage 4 frostbite.

13. The method of claim 1, wherein the pre-dilution composition is in a single dose vial in an amount of about 1 mL.

14. A method of treating severe frostbite in a subject, comprising
  a) diluting about 1 mL of a pre-dilution composition comprising a concentrated solution of iloprost, said concentrated solution of iloprost comprising (i) about 0.1 mg/mL of iloprost, or a pharmaceutically acceptable salt or a stercoisomer thereof, (ii) about 0.24 mg/mL of tromethamine, (iii) sodium chloride, and (iv) about 8.1 mg/mL of ethanol, in 0.9% sodium chloride, said diluted composition having a final concentration of about 1 µg/mL of iloprost, or a pharmaceutically acceptable salt or a stereoisomer thereof; and
  b) administering the diluted composition to the subject by intravenous infusion, wherein the administration comprises a titration step on a first day of administration, said titration step being repeated on the second and third days of administration;

wherein the administration on the first day comprises a starting dose and increments by which the dose is increased to a maximum dose, and wherein the administration on the second and third days comprises the same starting dose and increments of increase as on the first day, but wherein the maximum dose achieved on each day may be different wherein the diluted composition is administered to the subject for a maximum of 8 consecutive days; and wherein the method reduces the risk of digit amputation in the subject when compared with standard of care treatments for severe frostbite.

15. A method of treating severe frostbite in a subject comprising
  a) diluting about 1 mL of a pre-dilution composition comprising a concentrated solution of iloprost, said concentrated solution of iloprost comprising (i) about 0.1 mg/mL of iloprost, or a pharmaceutically acceptable salt or a stereoisomer thereof, (ii) about 0.24 mg/mL of tromethamine, (iii) sodium chloride, and (iv) about 8.1 mg/mL of ethanol, in 0.9% sodium chloride, said diluted composition having a final concentration of about 1 µg/mL of iloprost, or a pharmaceutically acceptable salt or a stereoisomer thereof, wherein the composition has a pH of 8.3; and
  b) administering the diluted composition to the subject by intravenous infusion, wherein the administration comprises a titration step on a first day of administration, said titration step being repeated on the second and third days of administration;

wherein the administration on the first day comprises a starting dose and increments by which the dose is increased to a maximum dose, and wherein the administration on the second and third days comprises the same starting dose and increments of increase as on the first day, but wherein the maximum dose achieved on each day may be different;

wherein the diluted composition is administered to the subject for a maximum of 8 consecutive days; and wherein the method reduces the risk of digit amputation in the subject when compared with standard of care treatments for severe frostbite.

16. The method of claim 1, wherein the pre-dilution composition comprises about 0.242 mg/mL of tromethamine.

17. The method of claim 1, wherein the pre-dilution composition has a pH of about 8.3.

18. The method of claim 1, wherein the pre-dilution composition is formulated as a sterile solution.

19. The method of claim 1, wherein the pre-dilution composition comprises no preservatives.

20. The method of claim 1, wherein the diluted composition comprises about 100 mL of the 0.9% sodium chloride.

21. The method of claim 1, wherein the diluting is performed in an IV bag.

22. The method of claim 21, wherein the infusion bag comprises about 100 mL of the 0.9% sodium chloride.

23. The method of claim 21, wherein the infusion bag is made of polyvinyl chloride (PVC).

24. The method of claim 1, wherein the method reduces the risk of digit amputation by at least 15%, at least 20%, at least 25%, or at least 30% when compared with standard of care treatments for frostbite.

25. The method of claim 1, wherein the method reduces the risk of digit amputation by about 35% to about 50% when compared with standard of care treatments for severe frostbite.

26. The method of claim 25, wherein the method reduces the risk of digit amputation by about 40% when compared with standard of care treatments for severe frostbite.

27. The method of claim 12, wherein the stage 3 frostbite is characterized by the presence of at least one digit of the subject having a lesion that extends just beyond a proximal phalanx.

28. The method of claim 12, wherein the stage 4 frostbite is characterized by the presence of at least one digit of the subject having a lesion extending proximal to a metacarpal joint or a metatarsal joint.

* * * * *